US006060200A

United States Patent [19]
Nohr et al.

[11] Patent Number: 6,060,200
[45] Date of Patent: May 9, 2000

[54] PHOTO-ERASABLE DATA PROCESSING FORMS AND METHODS

[75] Inventors: Ronald S. Nohr, Alpharetta; John Gavin MacDonald, Decatur, both of Ga.; Michael Wilfred Mosehauer, Loveland, Colo.

[73] Assignee: Kimberly-Clark Worldwide, Inc., Neenah, Wis.

[21] Appl. No.: 09/018,129

[22] Filed: Feb. 3, 1998

Related U.S. Application Data

[63] Continuation of application No. 08/777,996, Jan. 2, 1997, Pat. No. 5,733,693, which is a continuation of application No. 08/453,912, May 30, 1995, abandoned, which is a division of application No. 08/360,501, Dec. 21, 1994, Pat. No. 5,865,471, which is a continuation-in-part of application No. 08/258,858, Jun. 13, 1994, abandoned, which is a continuation-in-part of application No. 08/119,912, Sep. 10, 1993, abandoned, which is a continuation-in-part of application No. 08/103,503, Aug. 5, 1993, abandoned.

[51] Int. Cl.$^7$ ............................................... G03C 11/00
[52] U.S. Cl. ........................... 430/19; 430/21; 430/339; 283/85
[58] Field of Search ............................ 430/19, 21, 339; 283/85, 72; 347/264; 434/363; 427/162, 164, 553

[56] References Cited

U.S. PATENT DOCUMENTS

| | | |
|---|---|---|
| Re. 28,225 | 11/1974 | Heseltine et al. . |
| Re. 28,789 | 4/1976 | Chang . |
| 575,228 | 1/1897 | von Gallois . |
| 582,853 | 5/1897 | Feer . |
| 893,636 | 7/1908 | Maywald . |
| 1,013,544 | 1/1912 | Fuerth . |
| 1,325,971 | 12/1919 | Akashi . |
| 1,364,406 | 1/1921 | Olsen . |
| 1,436,856 | 11/1922 | Brenizer et al. . |
| 1,744,149 | 1/1930 | Staehlin . |
| 1,803,906 | 5/1931 | Krieger et al. . |
| 1,844,199 | 2/1932 | Bicknell et al. . |
| 1,876,880 | 9/1932 | Drapal . |
| 1,880,572 | 10/1932 | Wendt et al. . |
| 1,880,573 | 10/1932 | Wendt et al. . |
| 1,916,350 | 7/1933 | Wendt et al. . |
| 1,916,779 | 7/1933 | Wendt et al. . |
| 1,955,898 | 4/1934 | Wendt et al. . |

(List continued on next page.)

FOREIGN PATENT DOCUMENTS

| | | |
|---|---|---|
| 103085 | 4/1937 | Australia . |
| 12624/88 | 9/1988 | Australia . |
| 620075 | 5/1962 | Belgium . |
| 637169 | 3/1964 | Belgium . |
| 413257 | 10/1932 | Canada . |
| 458808 | 12/1936 | Canada . |
| 460268 | 10/1949 | Canada . |
| 461082 | 11/1949 | Canada . |
| 463021 | 2/1950 | Canada . |

(List continued on next page.)

OTHER PUBLICATIONS

Kubat et al. "Photophysical properties of metal complexes of meso–tetrakis (4Osulphonatophenyl) porphyrin," *J. Photochem. and Photobiol.* 96 93–97 1996.

Abstract for WO 95/00343—A1 *Textiles: Paper: Cellulose* p. 7 1995.

Maki, Y. et al. "A novel heterocyclic N–oxide, pyrimido[5, 4–g]pteridinetetrone 5–oxide, with multifunctional photo-oxidative properties" *Chemical Abstracts* 122 925 [No. 122:31350F] 1995.

Abstract of patent, JP 6–80915 (Canon Inc.), Mar. 22, 1994.

Abstract of patent, JP 06–43573 (Iku Meji) (Feb. 18, 1994.

Pitchumani, K. et al. "Modification of chemical reactivity upon cyclodextrin encapsulation" *Chemical Abstracts* 121 982 [No. 121:133624v] 1994.

Derwent Publications Ltd., London, JP 05297627 (Fujitsu Ltd.), Nov. 12, 1993. (Abstract).

Patent Abstracts of Japan, JP 5241369 (Bando Chem Ind Ltd et al.), Sep. 21, 1993. (Abstract).

Derwent Publications Ltd., London, JP 05232738 (Yamazaki, T.), Sep. 10, 1993. (Abstract).

Derwent Publications Ltd., London, EP 000559310 (Zeneca Ltd.), Sep. 8, 1993. (Abstract).

Derwent Publications Ltd., London, J,A, 5–230410 (Seiko Epson Corp), Sep. 7, 1993. (Abstract).

Derwent Publications Ltd., London, JP 5–230407 (Mitsubishi Kasei Corp), Sep. 7, 1993. (Abstract).

Abstract Of Patent, JP 405230410 (Seiko Epson Corp.), Sep. 7, 1993. (Abstract).

(List continued on next page.)

*Primary Examiner*—John A. McPherson
*Attorney, Agent, or Firm*—Jones & Askew, LLP

[57] ABSTRACT

A data processing form for use with photo-sensing apparatus that detect the presence of indicia at indicia-receiving locations on the form. The form is composed of a sheet of carrier material and plurality of indicia-receiving locations. The indicia-receiving locations are defined by a mutable colored composition including a mutable colorant and an ultraviolet radiation transorber such that the indicia-receiving locations are adapted to become substantially undetectable by photo-sensing apparatus upon irradiating the colored composition with ultraviolet radiation at a dosage level sufficient to irreversibly mutate the colorant. The colored composition may be irradiated with radiation in the ultraviolet region of the ultraviolet spectrum. Also disclosed is a data processing form that includes a plurality of mutable indicia, at least a portion of which are adapted to become substantially undetectable by photo-sensing apparatus upon irradiation with an effective dosage level of ultraviolet radiation such as, for example, ultraviolet radiation. One embodiment of the present invention encompasses a method for improving the readability of a data processing form used in photo-sensing apparatus. Another embodiment of the present invention encompasses a method of modifying indicia on a data processing form used in photo-sensing apparatus.

28 Claims, 8 Drawing Sheets

U.S. PATENT DOCUMENTS

| | | |
|---|---|---|
| 1,962,111 | 6/1934 | Bamberger . |
| 2,005,378 | 6/1935 | Kiel . |
| 2,005,511 | 6/1935 | Stoll et al. . |
| 2,049,005 | 7/1936 | Gaspar . |
| 2,054,390 | 9/1936 | Rust et al. . |
| 2,058,489 | 10/1936 | Murch et al. . |
| 2,062,304 | 12/1936 | Gaspar . |
| 2,090,511 | 8/1937 | Crossley et al. . |
| 2,097,119 | 10/1937 | Eggert . |
| 2,106,539 | 1/1938 | Schnitzspahn . |
| 2,111,692 | 3/1938 | Saunders et al. . |
| 2,125,015 | 7/1938 | Gaspar . |
| 2,130,572 | 9/1938 | Wendt . |
| 2,132,154 | 10/1938 | Gaspar . |
| 2,145,960 | 2/1939 | Wheatley et al. . |
| 2,154,996 | 4/1939 | Rawling . |
| 2,159,280 | 5/1939 | Mannes et al. . |
| 2,171,976 | 9/1939 | Erickson . |
| 2,181,800 | 11/1939 | Crossley et al. . |
| 2,185,153 | 12/1939 | Lecher et al. . |
| 2,220,178 | 11/1940 | Schneider . |
| 2,230,590 | 2/1941 | Eggert et al. . |
| 2,237,885 | 4/1941 | Markush et al. . |
| 2,243,630 | 5/1941 | Houk et al. . |
| 2,268,324 | 12/1941 | Polgar . |
| 2,281,895 | 5/1942 | van Poser et al. . |
| 2,328,166 | 8/1943 | Poigar et al. . |
| 2,346,090 | 4/1944 | Staehle . |
| 2,349,090 | 5/1944 | Haddock . |
| 2,356,618 | 8/1944 | Rossander et al. . |
| 2,361,301 | 10/1944 | Libby, Jr. et al. . |
| 2,364,359 | 12/1944 | Kienle et al. . |
| 2,381,145 | 8/1945 | von Glahn et al. . |
| 2,382,904 | 8/1945 | Federsen . |
| 2,386,646 | 10/1945 | Adams et al. . |
| 2,402,106 | 6/1946 | von Glahn et al. . |
| 2,416,145 | 2/1947 | Biro . |
| 2,477,165 | 7/1949 | Bergstrom . |
| 2,527,347 | 10/1950 | Bergstrom . |
| 2,580,461 | 1/1952 | Pearl . |
| 2,601,669 | 6/1952 | Tullsen . |
| 2,612,494 | 9/1952 | von Glahn et al. . |
| 2,612,495 | 9/1952 | von Glahn et al. . |
| 2,628,959 | 2/1953 | von Glahn et al. . |
| 2,647,080 | 7/1953 | Joyce . |
| 2,680,685 | 6/1954 | Ratchford . |
| 2,728,784 | 12/1955 | Tholstrup et al. . |
| 2,732,301 | 1/1956 | Robertson et al. . |
| 2,744,103 | 5/1956 | Koch . |
| 2,757,090 | 7/1956 | Meugebauer et al. . |
| 2,763,550 | 9/1956 | Lovick . |
| 2,768,171 | 10/1956 | Clarke et al. . |
| 2,773,056 | 12/1956 | Helfaer . |
| 2,798,000 | 7/1957 | Monterman . |
| 2,809,189 | 10/1957 | Stanley et al. . |
| 2,827,358 | 3/1958 | Kaplan et al. . |
| 2,834,773 | 5/1958 | Scalera et al. . |
| 2,875,045 | 2/1959 | Lurie . |
| 2,892,865 | 6/1959 | Giraldi et al. . |
| 2,897,187 | 7/1959 | Koch . |
| 2,936,241 | 5/1960 | Sharp et al. . |
| 2,940,853 | 6/1960 | Sagura et al. . |
| 2,955,067 | 10/1960 | McBurney et al. . |
| 2,992,129 | 7/1961 | Gauthier . |
| 2,992,198 | 7/1961 | Funahashi . |
| 3,030,208 | 4/1962 | Schellenberg et al. . |
| 3,071,815 | 1/1963 | MacKinnon . |
| 3,075,014 | 1/1963 | Palopoli et al. . |
| 3,076,813 | 2/1963 | Sharp . |
| 3,104,973 | 9/1963 | Sprague et al. . |
| 3,114,634 | 12/1963 | Brown et al. . |
| 3,121,632 | 2/1964 | Sprague et al. . |
| 3,123,647 | 3/1964 | Duennenberger et al. . |
| 3,133,049 | 5/1964 | Hertel et al. . |
| 3,140,949 | 7/1964 | Sprague et al. . |
| 3,154,416 | 10/1964 | Fidelman . |
| 3,155,509 | 11/1964 | Roscow . |
| 3,175,905 | 3/1965 | Wiesbaden . |
| 3,178,285 | 4/1965 | Anderau et al. . |
| 3,238,163 | 3/1966 | O'Neill . |
| 3,242,215 | 3/1966 | Heitmiller . |
| 3,248,337 | 4/1966 | Zirker et al. . |
| 3,266,973 | 8/1966 | Crowley . |
| 3,282,886 | 11/1966 | Gadecki . |
| 3,284,205 | 11/1966 | Sprague et al. . |
| 3,300,314 | 1/1967 | Rauner et al. . |
| 3,304,297 | 2/1967 | Wegmann et al. . |
| 3,305,361 | 2/1967 | Gaynor et al. . |
| 3,313,797 | 4/1967 | Kissa . |
| 3,320,080 | 5/1967 | Mazzarella et al. . |
| 3,330,659 | 7/1967 | Wainer . |
| 3,341,492 | 9/1967 | Champ et al. . |
| 3,359,109 | 12/1967 | Harder et al. . |
| 3,361,827 | 1/1968 | Biletch . |
| 3,363,969 | 1/1968 | Brooks . |
| 3,385,700 | 5/1968 | Willems et al. . |
| 3,397,984 | 8/1968 | Williams et al. . |
| 3,415,875 | 12/1968 | Luethi et la. . |
| 3,418,118 | 12/1968 | Thommes et al. . |
| 3,445,234 | 5/1969 | Cescon et al. . |
| 3,453,258 | 7/1969 | Parmerter et al. . |
| 3,453,259 | 7/1969 | Parmerter et al. . |
| 3,464,841 | 9/1969 | Skofronick . |
| 3,467,647 | 9/1969 | Benninga . |
| 3,479,185 | 11/1969 | Chambers . |
| 3,502,476 | 3/1970 | Kohei et al. . |
| 3,503,744 | 3/1970 | Itano et al. . |
| 3,514,597 | 5/1970 | Haes et al. . |
| 3,541,142 | 11/1970 | Cragoe, Jr. . |
| 3,546,161 | 12/1970 | Wolheim . |
| 3,547,646 | 12/1970 | Hori et al. . |
| 3,549,367 | 12/1970 | Chang et al. . |
| 3,553,710 | 1/1971 | Lloyd et al. . |
| 3,563,931 | 2/1971 | Horiguchi . |
| 3,565,753 | 2/1971 | Yurkowitz . |
| 3,574,624 | 4/1971 | Reynolds et al. . |
| 3,579,533 | 5/1971 | Yalman . |
| 3,595,655 | 7/1971 | Robinson et al. . |
| 3,595,657 | 7/1971 | Robinson et al. . |
| 3,595,658 | 7/1971 | Gerlach et al. . |
| 3,595,659 | 7/1971 | Gerlach et al. . |
| 3,607,639 | 9/1971 | Krefeld et al. . |
| 3,607,693 | 9/1971 | Heine et al. . |
| 3,607,863 | 9/1971 | Dosch . |
| 3,615,562 | 10/1971 | Harrison et al. . |
| 3,617,288 | 11/1971 | Hartman et al. . |
| 3,617,335 | 11/1971 | Kumura et al. . |
| 3,619,238 | 11/1971 | Kimura et al. . |
| 3,619,239 | 11/1971 | Osada et al. . |
| 3,637,337 | 1/1972 | Pilling . |
| 3,637,581 | 1/1972 | Horioguchi et al. . |
| 3,642,472 | 2/1972 | Mayo . |
| 3,647,467 | 3/1972 | Grubb . |
| 3,652,275 | 3/1972 | Baum et al. . |
| 3,660,542 | 5/1972 | Adachi et al. . |
| 3,667,954 | 6/1972 | Itano et al. . |
| 3,668,188 | 6/1972 | King et al. . |
| 3,669,925 | 6/1972 | King et al. . |
| 3,671,096 | 6/1972 | Mackin . |
| 3,671,251 | 6/1972 | Houle et al. . |
| 3,676,690 | 7/1972 | McMillin et al. . |
| 3,678,044 | 7/1972 | Adams . |

| | | |
|---|---|---|
| 3,689,565 | 9/1972 | Hoffmann et al. . |
| 3,694,241 | 9/1972 | Guthrie et al. . |
| 3,695,879 | 10/1972 | Laming et al. . |
| 3,697,280 | 10/1972 | Strilko . |
| 3,705,043 | 12/1972 | Zablak . |
| 3,707,371 | 12/1972 | Files . |
| 3,729,313 | 4/1973 | Smith . |
| 3,737,628 | 6/1973 | Azure . |
| 3,765,896 | 10/1973 | Fox . |
| 3,775,130 | 11/1973 | Enomoto et al. . |
| 3,788,849 | 1/1974 | Taguchi et al. . |
| 3,799,773 | 3/1974 | Watarai et al. . |
| 3,800,439 | 4/1974 | Sokolski et al. . |
| 3,801,329 | 4/1974 | Sandner et al. . |
| 3,817,752 | 6/1974 | Laridon et al. . |
| 3,840,338 | 10/1974 | Zviak et al. . |
| 3,844,790 | 10/1974 | Chang et al. . |
| 3,870,524 | 3/1975 | Watanabe et al. . |
| 3,873,500 | 3/1975 | Kato et al. . |
| 3,876,496 | 4/1975 | Lozano . |
| 3,887,450 | 6/1975 | Gilano et al. . |
| 3,895,949 | 7/1975 | Akamatsu . |
| 3,901,779 | 8/1975 | Mani . |
| 3,910,993 | 10/1975 | Avar et al. . |
| 3,914,165 | 10/1975 | Gaske . |
| 3,914,166 | 10/1975 | Rudolph et al. . |
| 3,915,824 | 10/1975 | McGinniss . |
| 3,919,323 | 11/1975 | Houlihan et al. . |
| 3,926,641 | 12/1975 | Rosen . |
| 3,928,264 | 12/1975 | Young, Jr. et al. . |
| 3,933,682 | 1/1976 | Bean . |
| 3,952,129 | 4/1976 | Matsukawa et al. . |
| 3,960,685 | 6/1976 | Sano et al. . |
| 3,965,157 | 6/1976 | Harrison . |
| 3,978,132 | 8/1976 | Houlihan et al. . |
| 3,984,248 | 10/1976 | Sturmer . |
| 3,988,154 | 10/1976 | Sturmer . |
| 4,004,998 | 1/1977 | Rosen . |
| 4,012,256 | 3/1977 | Levinos . |
| 4,017,652 | 4/1977 | Gruber . |
| 4,022,674 | 5/1977 | Rosen . |
| 4,024,324 | 5/1977 | Sparks . |
| 4,039,332 | 8/1977 | Kokelenberg et al. . |
| 4,043,819 | 8/1977 | Baumann . |
| 4,048,034 | 9/1977 | Martan . |
| 4,054,719 | 10/1977 | Cordes, III . |
| 4,056,665 | 11/1977 | Tayler et al. . |
| 4,058,400 | 11/1977 | Crivello . |
| 4,067,892 | 1/1978 | Thorne et al. . |
| 4,071,424 | 1/1978 | Dart et al. . |
| 4,073,968 | 2/1978 | Miyamoto et al. . |
| 4,077,769 | 3/1978 | Garcia . |
| 4,079,183 | 3/1978 | Green . |
| 4,085,062 | 4/1978 | Virgilio et al. . |
| 4,090,877 | 5/1978 | Streeper . |
| 4,100,047 | 7/1978 | McCarty . |
| 4,105,572 | 8/1978 | Gorondy . |
| 4,107,733 | 8/1978 | Schickedanz . |
| 4,110,112 | 8/1978 | Roman et al. . |
| 4,111,699 | 9/1978 | Krueger . |
| 4,114,028 | 9/1978 | Baio et al. . |
| 4,126,412 | 11/1978 | Masson et al. . |
| 4,141,807 | 2/1979 | Via . |
| 4,144,156 | 3/1979 | Kuesters et al. . |
| 4,148,658 | 4/1979 | Kondoh et al. . |
| 4,162,162 | 7/1979 | Dueber . |
| 4,171,977 | 10/1979 | Hasegawa et al. . |
| 4,179,577 | 12/1979 | Green . |
| 4,181,807 | 1/1980 | Green . |
| 4,190,671 | 2/1980 | Vanstone et al. . |
| 4,197,080 | 4/1980 | Mee . |
| 4,199,420 | 4/1980 | Photis . |
| 4,229,172 | 10/1980 | Baumann et al. . |
| 4,232,106 | 11/1980 | Iwasaki et al. . |
| 4,238,492 | 12/1980 | Majoie . |
| 4,239,843 | 12/1980 | Hara et al. . |
| 4,239,850 | 12/1980 | Kita et al. . |
| 4,241,155 | 12/1980 | Hara et al. . |
| 4,242,430 | 12/1980 | Hara et al. . |
| 4,242,431 | 12/1980 | Hara et al. . |
| 4,245,018 | 1/1981 | Hara et al. . |
| 4,245,995 | 1/1981 | Hugl et al. . |
| 4,246,330 | 1/1981 | Hara et al. . |
| 4,248,949 | 2/1981 | Hara et al. . |
| 4,250,096 | 2/1981 | Kvita et al. . |
| 4,251,622 | 2/1981 | Kimoto et al. . |
| 4,254,195 | 3/1981 | Hara et al. . |
| 4,256,493 | 3/1981 | Yokoyama et al. . |
| 4,256,817 | 3/1981 | Hara et al. . |
| 4,258,123 | 3/1981 | Nagashima et al. . |
| 4,258,367 | 3/1981 | Mansukhani . |
| 4,259,432 | 3/1981 | Kondoh et al. . |
| 4,262,936 | 4/1981 | Miyamoto . |
| 4,268,605 | 5/1981 | Hara et al. . |
| 4,268,667 | 5/1981 | Anderson . |
| 4,269,926 | 5/1981 | Hara et al. . |
| 4,270,130 | 5/1981 | Houle et al. . |
| 4,271,252 | 6/1981 | Hara et al. . |
| 4,271,253 | 6/1981 | Hara et al. . |
| 4,272,244 | 6/1981 | Schlick . |
| 4,276,211 | 6/1981 | Singer et al. . |
| 4,277,497 | 7/1981 | Fromantin . |
| 4,279,653 | 7/1981 | Makishima et al. . |
| 4,279,982 | 7/1981 | Iwasaki et al. . |
| 4,279,985 | 7/1981 | Nonogaki et al. . |
| 4,284,485 | 8/1981 | Berner . |
| 4,288,631 | 9/1981 | Ching . |
| 4,289,844 | 9/1981 | Specht et al. . |
| 4,290,870 | 9/1981 | Kondoh et al. . |
| 4,293,458 | 10/1981 | Gruenberger et al. . |
| 4,298,679 | 11/1981 | Shinozaki et al. . |
| 4,300,123 | 11/1981 | McMillin et al. . |
| 4,301,223 | 11/1981 | Nakamura et al. . |
| 4,302,606 | 11/1981 | Barabas et al. . |
| 4,306,014 | 12/1981 | Kunikane et al. . |
| 4,307,182 | 12/1981 | Dalzell et al. . |
| 4,308,400 | 12/1981 | Felder et al. . |
| 4,315,807 | 2/1982 | Felder et al. . |
| 4,318,705 | 3/1982 | Nowak et al. . |
| 4,318,791 | 3/1982 | Felder et al. . |
| 4,321,118 | 3/1982 | Felder et al. . |
| 4,335,054 | 6/1982 | Blaser et al. . |
| 4,335,055 | 6/1982 | Blaser et al. . |
| 4,336,323 | 6/1982 | Winslow . |
| 4,343,891 | 8/1982 | Aasen et al. . |
| 4,345,011 | 8/1982 | Drexhage . |
| 4,347,111 | 8/1982 | Gehlhaus et al. . |
| 4,349,617 | 9/1982 | Kawashiri et al. . |
| 4,350,753 | 9/1982 | Shelnut et al. . |
| 4,351,893 | 9/1982 | Anderson . |
| 4,356,255 | 10/1982 | Tachikawa et al. . |
| 4,357,468 | 11/1982 | Szejtli et al. . |
| 4,359,524 | 11/1982 | Masuda et al. . |
| 4,362,806 | 12/1982 | Whitmore . |
| 4,367,072 | 1/1983 | Vogtle et al. . |
| 4,367,280 | 1/1983 | Kondo et al. . |
| 4,369,283 | 1/1983 | Altschuler . |
| 4,370,401 | 1/1983 | Winslow et al. . |
| 4,372,582 | 2/1983 | Geisler . |
| 4,373,017 | 2/1983 | Masukawa et al. . |
| 4,373,020 | 2/1983 | Winslow . |
| 4,374,984 | 2/1983 | Eichler et al. . |
| 4,376,887 | 3/1983 | Greenaway et al. . |
| 4,383,835 | 5/1983 | Preuss et al. . |

| | | | | | | |
|---|---|---|---|---|---|---|
| 4,390,616 | 6/1983 | Sato et al. . | | 4,737,190 | 4/1988 | Shimada et al. . |
| 4,391,867 | 7/1983 | Derick et al. . | | 4,737,438 | 4/1988 | Ito et al. . |
| 4,399,209 | 8/1983 | Sanders et al. . | | 4,740,451 | 4/1988 | Kohara . |
| 4,400,173 | 8/1983 | Beavan . | | 4,745,042 | 5/1988 | Sasago et al. . |
| 4,401,470 | 8/1983 | Bridger . | | 4,746,735 | 5/1988 | Kruper, Jr. et al. . |
| 4,416,961 | 11/1983 | Drexhage . | | 4,752,341 | 6/1988 | Rock . |
| 4,421,559 | 12/1983 | Owatari . | | 4,755,450 | 7/1988 | Sanders et al. . |
| 4,424,325 | 1/1984 | Tsunoda et al. . | | 4,761,181 | 8/1988 | Suzuki . |
| 4,425,162 | 1/1984 | Sugiyama . | | 4,766,050 | 8/1988 | Jerry . |
| 4,425,424 | 1/1984 | Altland et al. . | | 4,766,055 | 8/1988 | Kawabata et al. . |
| 4,426,153 | 1/1984 | Libby et al. . | | 4,770,667 | 9/1988 | Evans et al. . |
| 4,434,035 | 2/1984 | Eichler et al. . | | 4,771,802 | 9/1988 | Tannenbaum . |
| 4,440,827 | 4/1984 | Miyamoto et al. . | | 4,772,291 | 9/1988 | Shibanai et al. . |
| 4,447,521 | 5/1984 | Tiers et al. . | | 4,772,541 | 9/1988 | Gottschalk . |
| 4,450,227 | 5/1984 | Holmes et al. . | | 4,775,386 | 10/1988 | Reinert et al. . |
| 4,460,676 | 7/1984 | Fabel . | | 4,786,586 | 11/1988 | Lee et al. . |
| 4,467,112 | 8/1984 | Matsuura et al. . | | 4,789,382 | 12/1988 | Neumann et al. . |
| 4,475,999 | 10/1984 | Via . | | 4,790,565 | 12/1988 | Steed . |
| 4,477,681 | 10/1984 | Gehlhaus et al. . | | 4,800,149 | 1/1989 | Gottschalk . |
| 4,489,334 | 12/1984 | Owatari . | | 4,803,008 | 2/1989 | Ciolino et al. . |
| 4,495,041 | 1/1985 | Goldstein . | | 4,808,189 | 2/1989 | Oishi et al. . |
| 4,496,447 | 1/1985 | Eichler et al. . | | 4,812,139 | 3/1989 | Brodmann . |
| 4,500,355 | 2/1985 | Shimada et al. . | | 4,812,517 | 3/1989 | West . |
| 4,508,570 | 4/1985 | Fugii et al. . | | 4,813,970 | 3/1989 | Kirjanov et al. . |
| 4,510,392 | 4/1985 | Litt et al. . | | 4,822,714 | 4/1989 | Sanders . |
| 4,523,924 | 6/1985 | Lacroix . | | 4,831,068 | 5/1989 | Reinert et al. . |
| 4,524,122 | 6/1985 | Weber et al. . | | 4,834,771 | 5/1989 | Yamauchi et al. . |
| 4,534,838 | 8/1985 | Lin et al. . | | 4,837,106 | 6/1989 | Ishikawa et al. . |
| 4,548,896 | 10/1985 | Sabongi et al. . | | 4,837,331 | 6/1989 | Yamanishi et al. . |
| 4,555,474 | 11/1985 | Kawamura . | | 4,838,938 | 6/1989 | Tomida et al. . |
| 4,557,730 | 12/1985 | Bennett et al. . | | 4,839,269 | 6/1989 | Okazaki et al. . |
| 4,564,560 | 1/1986 | Tani et al. . | | 4,849,320 | 7/1989 | Irving et al. . |
| 4,565,769 | 1/1986 | Dueber et al. . | | 4,853,037 | 8/1989 | Johnson et al. . |
| 4,567,171 | 1/1986 | Mangum . | | 4,853,398 | 8/1989 | Carr et al. . |
| 4,571,377 | 2/1986 | McGinniss et al. . | | 4,854,971 | 8/1989 | Gane et al. . |
| 4,595,745 | 6/1986 | Nakano et al. . | | 4,857,438 | 8/1989 | Loerzer et al. . |
| 4,604,344 | 8/1986 | Irving et al. . | | 4,861,916 | 8/1989 | Kohler et al. . |
| 4,605,442 | 8/1986 | Kawashita et al. . | | 4,865,942 | 9/1989 | Gottschalk et al. . |
| 4,613,334 | 9/1986 | Thomas et al. . | | 4,874,391 | 10/1989 | Reinert . |
| 4,614,723 | 9/1986 | Schmidt et al. . | | 4,874,899 | 10/1989 | Hoelderich et al. . |
| 4,617,380 | 10/1986 | Hinson et al. . | | 4,885,395 | 12/1989 | Hoelderich . |
| 4,620,875 | 11/1986 | Shimada et al. . | | 4,886,774 | 12/1989 | Doi . |
| 4,620,876 | 11/1986 | Fugii et al. . | | 4,892,941 | 1/1990 | Dolphin et al. . |
| 4,622,286 | 11/1986 | Sheets . | | 4,895,880 | 1/1990 | Gottschalk . |
| 4,631,085 | 12/1986 | Kawanishi et al. . | | 4,900,581 | 2/1990 | Stuke et al. . |
| 4,632,891 | 12/1986 | Banks et al. . | | 4,902,299 | 2/1990 | Anton . |
| 4,632,895 | 12/1986 | Patel et al. . | | 4,902,725 | 2/1990 | Moore . |
| 4,634,644 | 1/1987 | Irving et al. . | | 4,902,787 | 2/1990 | Freeman . |
| 4,638,340 | 1/1987 | Iiyama et al. . | | 4,911,732 | 3/1990 | Neumann et al. . |
| 4,647,310 | 3/1987 | Shimada et al. . | | 4,911,899 | 3/1990 | Hagiwara et al. . |
| 4,655,783 | 4/1987 | Reinert et al. . | | 4,917,956 | 4/1990 | Rohrbach . |
| 4,663,275 | 5/1987 | West et al. . | | 4,921,317 | 5/1990 | Suzuki et al. . |
| 4,663,641 | 5/1987 | Iiyama et al. . | | 4,925,770 | 5/1990 | Ichiura et al. . |
| 4,668,533 | 5/1987 | Miller . | | 4,925,777 | 5/1990 | Inoue et al. . |
| 4,672,041 | 6/1987 | Jain . | | 4,926,190 | 5/1990 | Lavar . |
| 4,698,291 | 10/1987 | Koibuchi et al. . | | 4,933,265 | 6/1990 | Inoue et al. . |
| 4,701,402 | 10/1987 | Patel et al. . | | 4,933,948 | 6/1990 | Herkstroeter . |
| 4,702,996 | 10/1987 | Griffing et al. . | | 4,937,161 | 6/1990 | Kita et al. . |
| 4,704,133 | 11/1987 | Reinert et al. . | | 4,942,113 | 7/1990 | Trundle . |
| 4,707,161 | 11/1987 | Thomas et al. . | | 4,944,988 | 7/1990 | Yasuda et al. . |
| 4,707,425 | 11/1987 | Sasagawa et al. . | | 4,950,304 | 8/1990 | Reinert et al. . |
| 4,707,430 | 11/1987 | Ozawa et al. . | | 4,952,478 | 8/1990 | Miyagawa et al. . |
| 4,711,668 | 12/1987 | Shimada et al. . | | 4,952,680 | 8/1990 | Schmeidl . |
| 4,713,113 | 12/1987 | Shimada et al. . | | 4,954,380 | 9/1990 | Kanome et al. . |
| 4,720,450 | 1/1988 | Ellis . | | 4,954,416 | 9/1990 | Wright et al. . |
| 4,721,531 | 1/1988 | Wildeman et al. . | | 4,956,254 | 9/1990 | Washizu et al. . |
| 4,721,734 | 1/1988 | Gehlhaus et al. . | | 4,964,871 | 10/1990 | Reinert et al. . |
| 4,724,021 | 2/1988 | Martin et al. . | | 4,965,294 | 10/1990 | Ohngemach et al. . |
| 4,724,201 | 2/1988 | Okazaki et al. . | | 4,966,607 | 10/1990 | Shinoki et al. . |
| 4,725,527 | 2/1988 | Robillard . | | 4,966,833 | 10/1990 | Inoue . |
| 4,727,824 | 3/1988 | Ducharme et al. . | | 4,968,596 | 11/1990 | Inoue et al. . |
| 4,732,615 | 3/1988 | Kawashita et al. . | | 4,968,813 | 11/1990 | Rule et al. . |

| | | | | | | |
|---|---|---|---|---|---|---|
| 4,985,345 | 1/1991 | Hayakawa et al. . | | 5,180,624 | 1/1993 | Kojima et al. . |
| 4,987,056 | 1/1991 | Imahashi et al. . | | 5,180,652 | 1/1993 | Yamaguchi et al. . |
| 4,988,561 | 1/1991 | Wason . | | 5,181,935 | 1/1993 | Reinert et al. . |
| 4,997,745 | 3/1991 | Kawamura et al. . | | 5,185,236 | 2/1993 | Shiba et al. . |
| 5,001,330 | 3/1991 | Koch . | | 5,187,045 | 2/1993 | Bonham et al. . |
| 5,002,853 | 3/1991 | Aoai et al. . | | 5,187,049 | 2/1993 | Sher et al. . |
| 5,002,993 | 3/1991 | West et al. . | | 5,190,565 | 3/1993 | Berenbaum et al. . |
| 5,003,142 | 3/1991 | Fuller . | | 5,190,710 | 3/1993 | Kletecka . |
| 5,006,758 | 4/1991 | Gellert et al. . | | 5,190,845 | 3/1993 | Hashimoto et al. . |
| 5,013,959 | 5/1991 | Kogelschatz . | | 5,193,854 | 3/1993 | Borowski, Jr et al. . |
| 5,017,195 | 5/1991 | Satou et al. . | | 5,196,295 | 3/1993 | Davis . |
| 5,023,129 | 6/1991 | Morganti et al. . | | 5,197,991 | 3/1993 | Rembold . |
| 5,025,036 | 6/1991 | Carson et al. . | | 5,198,330 | 3/1993 | Martic et al. . |
| 5,026,425 | 6/1991 | Hindagolla et al. . | | 5,202,209 | 4/1993 | Winnik et al. . |
| 5,026,427 | 6/1991 | Mitchell et al. . | | 5,202,210 | 4/1993 | Matsuoka et al. . |
| 5,028,262 | 7/1991 | Barlow, Jr. et al. . | | 5,202,211 | 4/1993 | Vercoulen . |
| 5,028,792 | 7/1991 | Mullis . | | 5,202,212 | 4/1993 | Shin et al. . |
| 5,030,243 | 7/1991 | Reinert . | | 5,202,213 | 4/1993 | Nakahara et al. . |
| 5,030,248 | 7/1991 | Meszaros . | | 5,202,215 | 4/1993 | Kanakura et al. . |
| 5,034,526 | 7/1991 | Bonham et al. . | | 5,202,221 | 4/1993 | Imai et al. . |
| 5,037,726 | 8/1991 | Kojima et al. . | | 5,205,861 | 4/1993 | Matrick . |
| 5,045,435 | 9/1991 | Adams et al. . | | 5,208,136 | 5/1993 | Zanoni et al. . |
| 5,045,573 | 9/1991 | Kohler et al. . | | 5,209,814 | 5/1993 | Felten et al. . |
| 5,047,556 | 9/1991 | Kohler et al. . | | 5,219,703 | 6/1993 | Bugner et al. . |
| 5,049,777 | 9/1991 | Mechtersheimer . | | 5,221,334 | 6/1993 | Ma et al. . |
| 5,053,320 | 10/1991 | Robbillard . | | 5,224,197 | 6/1993 | Zanoni et al. . |
| 5,055,579 | 10/1991 | Pawlowski et al. . | | 5,224,476 | 7/1993 | Schultz et al. . |
| 5,057,562 | 10/1991 | Reinert . | | 5,224,987 | 7/1993 | Matrick . |
| 5,068,364 | 11/1991 | Takagaki et al. . | | 5,226,957 | 7/1993 | Wickramanayake et al. . |
| 5,069,681 | 12/1991 | Bouwknegt et al. . | | 5,227,022 | 7/1993 | Leonhardt et al. . |
| 5,070,001 | 12/1991 | Stahlhofen . | | 5,241,059 | 8/1993 | Yoshinaga . |
| 5,073,448 | 12/1991 | Vieria et al. . | | 5,250,109 | 10/1993 | Chan et al. . |
| 5,074,885 | 12/1991 | Reinert . | | 5,254,429 | 10/1993 | Gracia et al. . |
| 5,076,808 | 12/1991 | Hahn et al. . | | 5,256,193 | 10/1993 | Winnik et al. . |
| 5,085,698 | 2/1992 | Ma et al. . | | 5,258,274 | 11/1993 | Helland et al. . |
| 5,087,550 | 2/1992 | Blum et al. . | | 5,261,953 | 11/1993 | Vieira et al. . |
| 5,089,050 | 2/1992 | Vieira et al. . | | 5,262,276 | 11/1993 | Kawamura . |
| 5,089,374 | 2/1992 | Saeva . | | 5,268,027 | 12/1993 | Chan et al. . |
| 5,096,456 | 3/1992 | Reinert et al. . | | 5,270,078 | 12/1993 | Walker et al. . |
| 5,096,489 | 3/1992 | Laver . | | 5,271,764 | 12/1993 | Winnik et al. . |
| 5,096,781 | 3/1992 | Vieira et al. . | | 5,271,765 | 12/1993 | Ma . |
| 5,098,477 | 3/1992 | Vieira et al. . | | 5,272,201 | 12/1993 | Ma et al. . |
| 5,098,793 | 3/1992 | Rohrbach et al. . | | 5,275,646 | 1/1994 | Marshall et al. . |
| 5,098,806 | 3/1992 | Robillard . | | 5,279,652 | 1/1994 | Kaufmann et al. . |
| 5,106,723 | 4/1992 | West et al. . | | 5,282,894 | 2/1994 | Albert et al. . |
| 5,108,505 | 4/1992 | Moffat . | | 5,284,734 | 2/1994 | Blum et al. . |
| 5,108,874 | 4/1992 | Griffing et al. . | | 5,286,286 | 2/1994 | Winnik et al. . |
| 5,110,706 | 5/1992 | Yumoto et al. . | | 5,286,288 | 2/1994 | Tobias et al. . |
| 5,110,709 | 5/1992 | Aoai et al. . | | 5,294,528 | 3/1994 | Furutachi . |
| 5,114,832 | 5/1992 | Zertani et al. . | | 5,296,275 | 3/1994 | Goman et al. . |
| 5,124,723 | 6/1992 | Laver . | | 5,296,556 | 3/1994 | Frihart . |
| 5,130,227 | 7/1992 | Wade et al. . | | 5,298,030 | 3/1994 | Burdeska et al. . |
| 5,133,803 | 7/1992 | Moffatt . | | 5,300,403 | 4/1994 | Angelopolus et al. . |
| 5,135,940 | 8/1992 | Belander et al. . | | 5,300,654 | 4/1994 | Nakajima et al. . |
| 5,139,572 | 8/1992 | Kawashima . | | 5,302,195 | 4/1994 | Helbrecht . |
| 5,139,687 | 8/1992 | Borgher, Sr. et al. . | | 5,302,197 | 4/1994 | Wickramanayke et al. . |
| 5,141,556 | 8/1992 | Matrick . | | 5,310,778 | 5/1994 | Shor et al. . |
| 5,141,797 | 8/1992 | Wheeler . | | 5,312,713 | 5/1994 | Yokoyama et al. . |
| 5,144,964 | 9/1992 | Demian . | | 5,312,721 | 5/1994 | Gesign . |
| 5,147,901 | 9/1992 | Rutsch et al. . | | 5,324,349 | 6/1994 | Sano et al. . |
| 5,153,104 | 10/1992 | Rossman et al. . | | 5,328,504 | 7/1994 | Ohnishi . |
| 5,153,105 | 10/1992 | Sher et al. . | | 5,330,860 | 7/1994 | Grot et al. . |
| 5,153,166 | 10/1992 | Jain et al. . | | 5,334,455 | 8/1994 | Noren et al. . |
| 5,160,346 | 11/1992 | Fuso et al. . | | 5,338,319 | 8/1994 | Kaschig et al. . |
| 5,160,372 | 11/1992 | Matrick . | | 5,340,631 | 8/1994 | Matsuzawa et al. . |
| 5,166,041 | 11/1992 | Murofushi et al. . | | 5,340,854 | 8/1994 | Martic et al. . |
| 5,169,436 | 12/1992 | Matrick . | | 5,344,483 | 9/1994 | Hinton . |
| 5,169,438 | 12/1992 | Matrick . | | 5,356,464 | 10/1994 | Hickman et al. . |
| 5,173,112 | 12/1992 | Matrick et al. . | | 5,362,592 | 11/1994 | Murofushi et al. . |
| 5,176,984 | 1/1993 | Hipps, Sr. et al. . | | 5,368,689 | 11/1994 | Agnemo . |
| 5,178,420 | 1/1993 | Shelby . | | 5,372,387 | 12/1994 | Wajda . |
| 5,180,425 | 1/1993 | Matrick et al. . | | 5,372,917 | 12/1994 | Tsuchida et al. . |

| | | |
|---|---|---|
| 5,374,335 | 12/1994 | Lindgren et al. . |
| 5,376,503 | 12/1994 | Audett et al. . |
| 5,383,961 | 1/1995 | Bauer et al. . |
| 5,384,186 | 1/1995 | Trinh . |
| 5,393,580 | 2/1995 | Ma et al. . |
| 5,401,303 | 3/1995 | Stoffel et al. . |
| 5,401,562 | 3/1995 | Akao . |
| 5,415,686 | 5/1995 | Kurabayashi et al. . |
| 5,415,976 | 5/1995 | Ali . |
| 5,424,407 | 6/1995 | Tanaka et al. . |
| 5,425,978 | 6/1995 | Berneth et al. . |
| 5,426,164 | 6/1995 | Babb et al. . |
| 5,427,415 | 6/1995 | Chang . |
| 5,429,628 | 7/1995 | Trinh et al. . |
| 5,431,720 | 7/1995 | Nagai et al. . |
| 5,432,274 | 7/1995 | Luong et al. . |
| 5,445,651 | 8/1995 | Thoen et al. . |
| 5,445,842 | 8/1995 | Anaka et al. . |
| 5,455,143 | 10/1995 | Ali . |
| 5,459,014 | 10/1995 | Nishijima et al. . |
| 5,464,472 | 11/1995 | Horn et al. . |
| 5,466,283 | 11/1995 | Kondo et al. . |
| 5,474,691 | 12/1995 | Severns . |
| 5,475,080 | 12/1995 | Gruber et al. . |
| 5,476,540 | 12/1995 | Shields et al. . |
| 5,479,949 | 1/1996 | Battard et al. . |
| 5,489,503 | 2/1996 | Toan . |
| 5,498,345 | 3/1996 | Jollenbeck et al. . |
| 5,501,774 | 3/1996 | Burke . |
| 5,503,664 | 4/1996 | Sano et al. . |
| 5,509,957 | 4/1996 | Toan et al. . |
| 5,531,821 | 7/1996 | Wu . |
| 5,532,112 | 7/1996 | Kohler et al. . |
| 5,541,633 | 7/1996 | Winnik et al. . |
| 5,543,459 | 8/1996 | Hartmann et al. . |
| 5,569,529 | 10/1996 | Becker et al. . |
| 5,571,313 | 11/1996 | Mafune et al. . |
| 5,575,891 | 11/1996 | Trokhan et al. . |
| 5,580,369 | 12/1996 | Belding et al. . |
| 5,591,489 | 1/1997 | Dragner et al. . |
| 5,607,803 | 3/1997 | Murofushi et al. . |
| 5,635,297 | 6/1997 | Ogawa et al. . |
| 5,643,631 | 7/1997 | Donigian et al. . |
| 5,672,392 | 9/1997 | De Clercq et al. . |
| 5,700,582 | 12/1997 | Sargeant et al. . |
| 5,705,247 | 1/1998 | Arai et al. . |
| 5,709,976 | 1/1998 | Malhotra . |

FOREIGN PATENT DOCUMENTS

| | | |
|---|---|---|
| 463022 | 2/1950 | Canada . |
| 465495 | 5/1950 | Canada . |
| 465496 | 5/1950 | Canada . |
| 465499 | 5/1950 | Canada . |
| 483214 | 5/1952 | Canada . |
| 517364 | 10/1955 | Canada . |
| 537687 | 3/1957 | Canada . |
| 552565 | 2/1958 | Canada . |
| 571792 | 3/1959 | Canada . |
| 779239 | 2/1968 | Canada . |
| 930103 | 7/1973 | Canada . |
| 2053094 | 4/1992 | Canada . |
| 94118 | 5/1958 | Czech Rep. . |
| 0223587 | 5/1957 | European Pat. Off. . |
| 0003884 | 9/1979 | European Pat. Off. . |
| 0029284 | 5/1981 | European Pat. Off. . |
| 0127574 | 12/1984 | European Pat. Off. . |
| 0262533 | 4/1988 | European Pat. Off. . |
| 0280458 | 8/1988 | European Pat. Off. . |
| 0308274 | 3/1989 | European Pat. Off. . |
| 0351615 | 1/1990 | European Pat. Off. . |
| 0371304 | 6/1990 | European Pat. Off. . |
| 0373662 | 6/1990 | European Pat. Off. . |
| 0375160 | 6/1990 | European Pat. Off. . |
| 0390439 | 10/1990 | European Pat. Off. . |
| 0458140A1 | 10/1991 | European Pat. Off. . |
| 0458140 | 11/1991 | European Pat. Off. . |
| 0468465 | 1/1992 | European Pat. Off. . |
| 0542286 | 5/1993 | European Pat. Off. . |
| 000571190 | 11/1993 | European Pat. Off. . |
| 0608433 | 8/1994 | European Pat. Off. . |
| 0609159 | 8/1994 | European Pat. Off. . |
| 0639664 | 2/1995 | European Pat. Off. . |
| 2245010 | 4/1975 | France . |
| 2383157 | 10/1978 | France . |
| 1047787 | 12/1957 | Germany . |
| 1022801 | 1/1958 | Germany . |
| 1039835 | 9/1958 | Germany . |
| 1040562 | 10/1958 | Germany . |
| 1045414 | 12/1958 | Germany . |
| 1047013 | 12/1958 | Germany . |
| 1132450 | 7/1962 | Germany . |
| 1132540 | 7/1962 | Germany . |
| 1154069 | 9/1963 | Germany . |
| 1240811 | 5/1967 | Germany . |
| 2202497 | 8/1972 | Germany . |
| 2432563 | 2/1975 | Germany . |
| 2437380 | 2/1975 | Germany . |
| 2444520 | 3/1975 | Germany . |
| 2416259 | 10/1975 | Germany . |
| 2714978 | 10/1977 | Germany . |
| 2722264 | 11/1978 | Germany . |
| 158237 | 1/1983 | Germany . |
| 3126433 | 1/1983 | Germany . |
| 3415033 | 10/1984 | Germany . |
| 271512 | 9/1989 | Germany . |
| 3921600 | 1/1990 | Germany . |
| 3833437 | 4/1990 | Germany . |
| 3833438 | 4/1990 | Germany . |
| 004036328 | 7/1991 | Germany . |
| 4132288 | 4/1992 | Germany . |
| 4126461 | 2/1993 | Germany . |
| 662500 | 4/1964 | Italy . |
| 42-4756 | 2/1967 | Japan . |
| 43-15663 | 7/1968 | Japan . |
| 47-26653 | 7/1972 | Japan . |
| 47-45409 | 11/1972 | Japan . |
| 49-8909 | 2/1974 | Japan . |
| 50-65592 | 6/1975 | Japan . |
| 51-17802 | 2/1976 | Japan . |
| 53-104321 | 9/1978 | Japan . |
| 55-62059 | 5/1980 | Japan . |
| 55-90506 | 7/1980 | Japan . |
| 56-8134 | 1/1981 | Japan . |
| 0014233 | 2/1981 | Japan . |
| 56-14569 | 2/1981 | Japan . |
| 56-24472 | 3/1981 | Japan . |
| 56-36556 | 4/1981 | Japan . |
| 57-61055 | 4/1982 | Japan . |
| 57-128283 | 8/1982 | Japan . |
| 57-171775 | 10/1982 | Japan . |
| 58-124452 | 7/1983 | Japan . |
| 58-125770 | 7/1983 | Japan . |
| 58-222164 | 12/1983 | Japan . |
| 59-89360 | 5/1984 | Japan . |
| 29219270 | 12/1984 | Japan . |
| 59-219270 | 4/1985 | Japan . |
| 60-192729 | 10/1985 | Japan . |
| 60-239739 | 11/1985 | Japan . |
| 60-239740 | 11/1985 | Japan . |
| 60-239741 | 11/1985 | Japan . |
| 60-239743 | 11/1985 | Japan . |
| 61-14994 | 1/1986 | Japan . |
| 61-14995 | 1/1986 | Japan . |
| 61-21184 | 1/1986 | Japan . |

| | | |
|---|---|---|
| 61-288 | 1/1986 | Japan . |
| 61-3781 | 1/1986 | Japan . |
| 61-25885 | 2/1986 | Japan . |
| 61-30592 | 2/1986 | Japan . |
| 61-40366 | 2/1986 | Japan . |
| 61-77846 | 4/1986 | Japan . |
| 61-128973 | 6/1986 | Japan . |
| 61-97025 | 9/1986 | Japan . |
| 61-222789 | 10/1986 | Japan . |
| 61-247703 | 11/1986 | Japan . |
| 61-285403 | 12/1986 | Japan . |
| 62-7703 | 1/1987 | Japan . |
| 62-100557 | 5/1987 | Japan . |
| 62-97881 | 5/1987 | Japan . |
| 62-127281 | 6/1987 | Japan . |
| 63-43959 | 2/1988 | Japan . |
| 63-48370 | 3/1988 | Japan . |
| 63-95439 | 4/1988 | Japan . |
| 63-95440 | 4/1988 | Japan . |
| 63-95445 | 4/1988 | Japan . |
| 63-95446 | 4/1988 | Japan . |
| 63-95447 | 4/1988 | Japan . |
| 63-95448 | 4/1988 | Japan . |
| 63-95449 | 4/1988 | Japan . |
| 63-95450 | 4/1988 | Japan . |
| 63-151946 | 6/1988 | Japan . |
| 63-164953 | 7/1988 | Japan . |
| 63-165498 | 7/1988 | Japan . |
| 63-223077 | 9/1988 | Japan . |
| 63-223078 | 9/1988 | Japan . |
| 63-243101 | 10/1988 | Japan . |
| 63-199781 | 12/1988 | Japan . |
| 64-15049 | 1/1989 | Japan . |
| 6429337 | 1/1989 | Japan . |
| 64-40948 | 2/1989 | Japan . |
| 89014948 | 3/1989 | Japan . |
| 1-128063 | 5/1989 | Japan . |
| 1146974 | 6/1989 | Japan . |
| 01210477 | 8/1989 | Japan . |
| 1288854 | 11/1989 | Japan . |
| 2-58573 | 2/1990 | Japan . |
| 292957 | 4/1990 | Japan . |
| 217642 | 7/1990 | Japan . |
| 2282261 | 11/1990 | Japan . |
| 3-134072 | 6/1991 | Japan . |
| 03163566 | 7/1991 | Japan . |
| 3-170415 | 7/1991 | Japan . |
| 3-206439 | 9/1991 | Japan . |
| 5134447 | 11/1991 | Japan . |
| 3-203694 | 12/1991 | Japan . |
| 3284668 | 12/1991 | Japan . |
| 4023884 | 1/1992 | Japan . |
| 4023885 | 1/1992 | Japan . |
| 4-45174 | 2/1992 | Japan . |
| 4100801 | 4/1992 | Japan . |
| 4-136075 | 5/1992 | Japan . |
| 04356087 | 12/1992 | Japan . |
| 543806 | 2/1993 | Japan . |
| 561220 | 3/1993 | Japan . |
| 5080506 | 4/1993 | Japan . |
| 05119506 | 5/1993 | Japan . |
| 5-140498 | 6/1993 | Japan . |
| 2-219869 | 9/1993 | Japan . |
| 5263067 | 10/1993 | Japan . |
| 680915 | 3/1994 | Japan . |
| 6116555 | 4/1994 | Japan . |
| 6116556 | 4/1994 | Japan . |
| 6116557 | 4/1994 | Japan . |
| 6-175584 | 6/1994 | Japan . |
| 6214339 | 8/1994 | Japan . |
| 6256494 | 9/1994 | Japan . |
| 6256633 | 9/1994 | Japan . |
| 7113828 | 4/1972 | Netherlands . |
| 603767 | 8/1978 | Switzerland . |
| 197808 | 5/1988 | Switzerland . |
| 1310767 | 5/1987 | U.S.S.R. . |
| 1772118 | 10/1992 | U.S.S.R. . |
| 275245 | 10/1928 | United Kingdom . |
| 349339 | 5/1931 | United Kingdom . |
| 355686 | 8/1931 | United Kingdom . |
| 399753 | 10/1933 | United Kingdom . |
| 441085 | 1/1936 | United Kingdom . |
| 463515 | 4/1937 | United Kingdom . |
| 492711 | 9/1938 | United Kingdom . |
| 518612 | 3/1940 | United Kingdom . |
| 539912 | 9/1941 | United Kingdom . |
| 626727 | 7/1947 | United Kingdom . |
| 600451 | 4/1948 | United Kingdom . |
| 616362 | 1/1949 | United Kingdom . |
| 618616 | 2/1949 | United Kingdom . |
| 779389 | 7/1957 | United Kingdom . |
| 1372884 | 11/1974 | United Kingdom . |
| 2146357 | 4/1985 | United Kingdom . |
| 92/11295 | 7/1992 | WIPO . |
| 93/06597 | 4/1993 | WIPO . |
| 94/01503 | 1/1994 | WIPO . |
| 94/22500 | 10/1994 | WIPO . |
| 94/22501 | 10/1994 | WIPO . |
| 95/04955 | 2/1995 | WIPO . |
| 96/00740 | 1/1996 | WIPO . |
| 96/19502 | 6/1996 | WIPO . |
| 96/22335 | 7/1996 | WIPO . |

OTHER PUBLICATIONS

Abstract Of Patent, JP 405230407 (Mitsubishi Kasei Corp.), Sep. 7, 1993. (Abstract).
Patent Abstracts of Japan, JP 5197198 (Bando Chem Ind Ltd et al.), Aug. 6, 1993. (Abstract).
Database WPI –Derwent Publications Ltd., London, J,A, 5197069 (Bando Chem), Aug. 6, 1993. (Abstract).
Abstract of patent, JP 5–195450 (Nitto Boseki Co. Ltd), Aug. 3, 1993.
Patent Abstracts of Japan, JP5181308 (Bando Chem Ind Ltd et al.), Jul. 23, 1993. (Abstract).
Patent Abstracts of Japan, JP 5181310 (Bando Chem Ind Ltd et al.), Jul. 23, 1993. (Abstract).
Derwent Publications Ltd., London, JP 5–132638 (Mitsubishi Kasei Corp), May 28, 1993. (Abstract).
Abstract Of Patent, JP 405132638 (Mitsubishi Kasei Corp.), May 28, 1993. (Abstract).
Derwent Publications Ltd., London, JP 5–125318 (Mitsubishi Kasei Corp), May 21, 1993. (Abstract).
Abstract Of Patent, JP 405125318 (Mitsubishi Kasei Corp.), May 21, 1993. (Abstract).
Abstract of patent, JP 05–117200 (Hidefumi Hirai et al.) (May 14, 1993).
Derwent World Patents Index, JP 5117105 (Mitsui Toatsu Chem Inc.) May 14, 1993.
Derwent Publications Ltd., London, JP 05061246 (Ricoh KK), Mar. 12, 1993. (Abstract).
Husain, N. et al. "Cyclodextrins as mobile–phase additives in reversed–phase HPLC" *American Laboratory* 82 80–87 1993.
Hamilton, D.P. "Tired of Shredding? New Ricoh Method Tries Different Tack" *Wall Street Journal* B2 1993.
"Cyclodextrins: A Breakthrough for Molecular Encapsulation" American Maize Products Co. (AMAIZO) 1993.
Duxbury "The Photochemistry and Photophysics of Triphenylmethane Dyes in Solid Liquid Media" *Chemical Review* 93 381–433 1993.

Abstract of patent, JP 04–351603 (Dec. 7, 1992).
Abstract of patent, JP 04–351602 1992.
Derwent Publications Ltd., London, JP 404314769 (Citizen Watch Co. Ltd.), Nov. 5, 1992. (Abstract).
Abstract of patent, JP 04315739 1992.
Derwent Publications Ltd., London, JP 04300395 (Funai Denki KK), Oct. 23, 1992. (Abstract).
Derwent Publications Ltd., London, JP 404213374 (Mitsubishi Kasei Corp), Aug. 4, 1992. (Abstract).
Abstract of patent, JP 04–210228 1992.
Abstract Of Patent, JP 404202571 (Canon Inc.), Jul. 23, 1992. (Abstract).
Abstract Of Patent, JP 404202271 (Mitsubishi Kasei Corp.), Jul. 23, 1992. (Abstract).
Derwent Publications Ltd., London, JP 4–189877 (Seiko Epson Corp), Jul. 8, 1992. (Abstract).
Derwent Publications Ltd., London, JP 404189876 (Seiko Epson Corp), Jul. 8, 1992. (Abstract).
Abstract Of Patent, JP 404189877 (Seiko Epson Corp.), Jul. 8, 1992. (Abstract).
Derwent Publications Ltd., London, J,A, 4–170479 (Seiko Epson Corp), Jun. 18, 1992. (Abstract).
Abstract of patent, JP 04–81402 1992.
Abstract of patent, JP 04–81401 1992.
Kogelschatz "Silent–discharge driven excimer UV sources and their applications" *Applied Surface Science* 410–423 1992.
Derwent Publications, Ltd., London, JP 403269167 (Japan Wool Textile KK), Nov. 29, 1991 (Abstract).
Derwent Publications Ltd., London, JO 3247676 (Canon KK), Nov. 5, 1991 (Abstract).
Abstract of patent, JP 03–220384 1991.
Patent Abstracts of Japan, JP 03184896 (Dainippon Printing Co Ltd.) Aug. 12, 1991.
Derwent Publications Ltd., London, JP 3167270 (Mitsubishi Kasei Corp), Jul. 19, 1991. (Abstract).
Derwent Publications Ltd., London, JO 3093870 (Dainippon Ink Chem KK.), Apr. 18, 1991 (Abstract).
Abstract of patent, JP 06369890 1991.
Kogelschatz, U. et al. "New Excimer UV Sources for Industrial Applications" *ABB Review* 1–10 1991.
Abstract of patent, JP 03–41165 1991.
"Coloring/Decoloring Agent for Tonor Use Developed" *Japan Chemical Week* 1991.
Braithwaite, M., et al. "Formulation" *Chemistry & Technology of UV & EB Formulation for Coatings, Inks & Paints* IV 11–12 1991.
*Scientific Polymer Products, Inc. Brochure* 24–31 1991.
Dietliker, K. "Photoiniators for Free Radical and Catioinc Polymerisation" *Chem & Tech of UV & EB Formulation for Coatings, Inks & Paints* III 280 1991.
Esrom et al. "Large area Photochemical Dry Etching of Polymers iwth Incoherent Excimer UV Radiation" *MRS Materials Research Society* 1–7 1991.
"New Excimer UV Sources for Industrial Applications" *ABB Review* 391 1–10 1991.
Esrom et al. Excimer Laser–Induced Decompostion of Aluminum Nitride *Materials Research Society Fall Meeting* 1–6 1991.
Esrom et al. "Metal deposition with a windowless VUV excimer source" *Applied Surface Science* 1–5 1991.
Esrom "Excimer Laser–Induced Surface Activation of Aln for Electroless Metal Deposition" *Mat. Res. Sco.lSymp. Proc.* 204 457–465 1991.

Zhang et al. "UV–induced decompositin of adsorbed Cu–acetylacetonate films at room temperature for electroless metal plating" *Applied Surface Science* 1–6 1991.
"Coloring/Decoloring Agent for Tonor Use Developed" *Japan Chemical Week* 1991.
"German company develops reuseable paper" *Pulp & Paper* 1991.
Abstract of patent, JP 02289652 1990.
Ohashi et al. "Molecular Mechanics Studies on Inclusion Compounds of Cyanine Dye Monomers and Dimers in Cyclodextrin Cavities," *J. Am. Chem. Soc.* 112 5824–5830 1990.
Kogelschatz et al. "New Incoherent Ultraviolet Excimer Sources for Photolytic Material Deposition," *Laser Und Optoelektronik* 1990.
Patent Abstracts of Japan, JP 02141287 (Dainippon Printing Co Ltd.) May 30, 1990.
Abstract of Patent, JP 0297957, (Fuji Xerox Co., Ltd.) 1990.
Derwent Publications Ltd., London, JP 2091166 (Canon KK), Mar. 30, 1990. (Abstract).
Esrom et al. "Metal Deposition with Incoherent Excimer Radiation" *Mat. Res. Soc. Symp. Proc.* 158 189–198 1990.
Esrom "UV Excimer Laer–Induced Deposition of Palladium from palladiym Acetate Films" *Mat. Res. Soc. Symp. Proc.* 158 109–117 1990.
Kogelschatz, U. "Silent Discharges for the Generation of ultraviolet and vacuum ultraviolet excimer radiation" *Pure & Applied Chem.* 62 1667–74 1990.
Esrom et al. "Investigation of the mechanism of the UV–induced palladium depostions processf from thin solid palladium acetate films" *Applied Surface Science* 46 158–162 1990.
Zhang et al. "VUV synchrotron radiation processing of thin palladium acetate spin–on films for metallic surface patterning" *Applied Surface Science* 46 153–157 1990.
Brennan et al. "Tereoelectronic effects in ring closure reactions: the 2'–hydroxychalcone—flavanone equilibrium, and related systems," *Canadian J. Chem.* 68 (10) pp. 1780–1785 1990.
Abstract of patent, JP 01–299083 1989.
Derwent Publications Ltd., London, J,O, 1182379 (Canon KK), Jul. 20, 1989. (Abstract).
Derwent Publications Ltd., London, JO 1011171 (Mitsubishi Chem Ind. KK.), Jan. 13, 1989 (Abstract).
Gruber, R.J., et al. "Xerographic Materials" *Encyclopedia of Polymer Science and Engineering* 17 918–943 1989.
Pappas, S.P. "Photocrosslinking" *Comph. Pol. Sci.* 6 135–148 1989.
Pappas, S.P. "Photoinitiated Polymerization" *Comph. Pol. Sci.* 4 337–355 1989.
Kirilenko, G.V. et al. "An analog of the vesicular process with amplitude modulation of the incident light beam" *Chemical Abstracts* 111 569 [No. 111:123633b] 1989.
Esrom et al. "UV excimer laser–induced pre–nucleation of surfaces followed by electroless metallization" *Chemtronics* 4 216–223 1989.
Esrom et al. "VUV light–induced depostion of palladium using an incoherent Xe2* excimer source" *Chemtronics* 4 1989.
Esrom et al. "UV Light–Induced Depostion of Copper Films" C5–719–C5–725 1989.
Falbe et al. *Rompp Chemie Lexikon* 9 270 1989.
Derwent Publications, Ltd., London, SU 1423656 (Kherson Ind Inst), Sep. 15, 1988 (Abstract).

Derwent Publications, Ltd., London, EP 0280653 (Ciba GeigyAG), Aug. 31, 1988 (Abstract).
Abstract of patent, JP 63–190815 1988.
Patent Abstracts of Japan, JP 63179985 (Tomoegawa Paper Co. Ltd.), Jul. 23, 1988.
Derwent World Patents Index, JP 63179977 (Tomoegawa Paper Mfg Co Ltd), Jul. 23, 1988.
Furcone, S.Y. et al. "Spin–on B14Sr3Ca3Cu4O16+x superconducting thin films from citrate precursors," *Appl. Phys. Lett.* 52(25) 2180–2182 1988.
Abstract of patent, JP 63–144329 1988.
Abstract of patent, JP 63–130164 1988.
Derwent Publications, Ltd., London, J6 3112770 (Toray Ind Inc), May 17, 1988 (Abstract).
Derwent Publications, Ltd., London, J6 3108074 (Konishiroku Photo KK), May 12, 1988 (Abstract).
Derwent Publications, Ltd., London,J6 3108073 (Konishiroku Photo KK), May 12, 1988 (Abstract).
Abstract of patent, JP 61–77846 1988.
Abstract of patent, JP 63–73241 1988.
Abstract of patent, JP 6347762, 1988.
Abstract of patent, JP 63–47763, 1988.
Abstract of patent, JP 63–47764, 1988.
Abstract of patent, JP 63–47765, 1988.
Eliasson, B., et al. "UV Excimer Radiation from Dielectric–Barrier Discharges" *Applied Physics B* 46 299–303 1988.
Eliasson et al. "New Trends in High Intensity UV Generation" *EPA Newsletter* (32) 29–40 1988.
Cotton, F.A. "Oxygen: Group Via(16)" *Advanced Inorganic Chemistry* 5th ed. 473–474 1988.
Derwent Publications, Ltd., London, J6 2270665 (Konishiroku Photo KK), Nov. 25, 1987 (Abstract).
Abstract of patent, JP 62–215261 1987.
Database WPI, Derwent Publications Ltd., London, JP 62032082 (Mitsubishi Denki KK), Feb. 12, 1987. (Abstract).
Abstract of patent, JP 62–32082 1987.
Derwent Publications Ltd., London, J6 2007772 (Alps Electric KK.), Jan. 14, 1987 (Abstract).
Gross et al. "Laser direct–write metallization in thin palladium acetate films" *J. App. Phys.* 61 (4) 1628–1632 1987.
Al–Ismail et al. "Some experimental results on thin polypropylene films loaded with finely–dispersed copper" *Journal of Materials Science* 415–418 1987.
Baufay et al. "Optical self–regulation during laser–induced oxidation of copper" *J. Appl. Phys* 61 (9) 4640–4651 1987.
Gross et al. "Laser direct–write metallization in thin palladium acetate films" *J. App. Phys.* 61 (4) 1628–1632 1987.
Derwent Publications Ltd., London, JA 0284478 (Sanyo Chem Ind Ltd.), Dec. 15, 1986 (Abstract).
Abstract of patent, JP 61251842 1986.
Database WPI, Derwent Publications Ltd., London, GB; SU, A, 1098210 (Kutulya L A) Jun. 23, 1986.
Abstract of patent, JP 61–97025 1986.
Abstract of patent, JP 61–87760 1986.
Derwent Publications Ltd., London, DL 0234731 (Karl Marx Univ. Leipzig), Apr. 9, 1986. (Abstract).
Derwent World Patents Index, SU 1219612 (As USSR Non–Aq Soln) Mar. 23, 1986.
Derwent Publications, Ltd., London, J6 1041381 (Osaka Prefecture), Feb. 27, 1986 (Abstract).
Dialog, JAPIO, JP 61–034057 (Ciba Geigy AG) Feb. 18, 1986.

Derwent World Patents Index, JP 61027288 (sumitomo Chem Ind KK) Feb. 6, 1986.
Sakai et al. "A Novel and Practical Synthetic Method of 3(2H)–Furanone Derivatives," *J. Heterocyclie Chem.* 23 pp. 1199–1201 1986.
Jellinek, H.H.G. et al. "Evolution of H2O and CO2 During the Copper–Catalyzed Oxidation of Isotactic Polypropylene," *J. Polymer Sci.* 24 389–403 1986.
Jellinek, H.H.G. et al. "Diffusion of Ca2+ Catalysts from Cu–Metal Polymer or Cu–Oxide/Polymer Interfaces into Isotactic Polypropylene," *J. Polymer Sci.* 24 503–510 1986.
John J. Eisch and Ramiro Sanchez "Selective, Oxophilic Imination of Ketones with Bis (dichloroaluminum) Phenylimide" *J. Org. Chem.* 51 (10) 1848–1852 1986.
Derwent Publications Ltd., London, J6 0226575 (Sumitomo Chem Ind Ltd.), Oct. 11, 1985 (Abstract).
Abstract of patent, JP 60–156761 1985.
Derwent Publications Ltd., London, J,A, 0011451 (Fugi Photo Film KK), Jan. 21, 1985. (Abstract).
Derwent Publications, Ltd., London J6 0011–449–A (Taoka Chemical KK) Jan. 21, 1985 (abstract).
Roos, G. et al. "Textile applications of photocrosslinkable polmyers" *Chemical Abstracts* 103 57 [No. 103:23690j] 1985.
Derwent World Patents Index, EP 127574 (Ciba Geigy AG), Dec. 5, 1984.
Derwent Publications Ltd., London, JP 0198187 (Canon KK), Nov. 9, 1984. (Abstract).
Derwent Publications Ltd., London, J,A, 0169883 (Ricoh KK), Sep. 25, 1984. (Abstract).
Derwent Publications Ltd., London, JA 0169883 (Ricoh KK), Sep. 25, 1984 (Abstract).
Derwent Publications Ltd., London, JA 0198187 (Canon KK), Sep. 11, 1984 (Abstract).
Derwent Publications Ltd., London, J,A, 0053563 (Dainippon Toryo KK), Mar. 28, 1984. (Abstract).
Derwent Publications Ltd., London, J,A, 0053562 (Dainippon Toryo KK), Mar. 28, 1984. (Abstract).
Abstract of Patent, JA 0053563 (Dainippon Toryo KK), Mar. 28, 1984 (Abstract).
Abstract of Patent, JA 0053562 (Dainippon Toryo KK), Mar. 28, 1984 (Abstract).
Derwent Publications Ltd., London, J,A, 0051961 (Dainippon Toryo KK), Mar. 26, 1984. (Abstract).
Abstract of Patent, JA 0051961 (Dainippon Toryo KK), Mar. 26, 1984 (Abstract).
Saenger, W. "Structural Aspects of Cyclodextrins and Their Inclusion Complexes" *Inclusion Compounds—Structural Aspects of Inclusion Compounds formed by Organic Host* 2 231–259 1984.
Szejtli "Industrial Applications of Cyclodextrins" *Inclusion Compounds: Physical Prop. & Applns* 3 331–390 1984.
Kano et al. "Three–Component Complexes of Cyclodextrins. Exciplex Formation in Cyclodextrin Cavity," *J. Inclusion Phenomena* 2 pp. 737–746 1984.
Suzuki et al. "Spectroscopic Investigation of Cyclodextrin Monomers, Derivatives, Polymers and Azo Dyes," *J. Inclusion Phenomena* 2, pp. 715–724 1984.
Abstract of Patent, JA 0222164 (Ricoh KK), Dec. 23, 1983 (Abstract).
Abstract of patent, JP 58211426 (Sekisui Plastics KK), (Dec. 8, 1983).
Derwent Publications, Ltd., London, EP 0072775 (Ciba Geigy AG), Feb. 23, 1983 (Abstract).

van Beek, H.C.A "Light–Induced Colour Changes in Dyes and Materials" *Color Res. and Appl.* 8 176–181 1983.

Connors, K.A. "Application of a stoichiometric model of cyclodextrin complex formation" *Chemical Abstracts* 98 598 [No. 98:53067g] 1983.

Abstract of Patent, EP 0065617 (IBM Corp.), Dec. 1, 1982 (Abstract).

Derwent Publications Ltd., London, J,A, 0187289 (Honshu Paper Mfg KK), Nov. 17, 1982. (Abstract).

Abstract of Patent, JA 0187289 (Honsho Paper Mfg KK), Nov. 17, 1982 (Abstract).

Abstract of Patent, JA 0185364 (Ricoh KK), Nov. 15, 1982 (Abstract).

Derwent Publications, Ltd., London J5 7139–146 (Showa Kako KK) Aug. 27, 1982(abstract).

Abstract of Patent, JA 0090069 (Canon KK), Jun. 4, 1982 (Abstract).

Derwent Publications, Ltd., London, JA 0061785 (Nippon Senka KK), Apr. 14, 1982 (Abstract).

Fischer, "Submicroscopic contact imaging with visible light by energy transfer" *Appl. Phys. Letter* 40(3) 1982.

Abstract of Patent, JA 0010659 (Canon KK), Jan. 2, 1982 (Abstract).

Abstract of Patent, JA 0010661 (Canon KK), Jan. 2, 1982 (Abstract).

Christen "Carbonylverbindungen: Aldehyde und Ketone," *Grundlagen der Organischen Chemie* 255 1982.

Derwent Publications Ltd., London, J,A, 0155263 (Canon KK), Dec. 1, 1981. (Abstract).

Abstract of Patent, JA 0155263 (Canon KK), Dec. 1, 1981 (Abstract).

Abstract of Patent, JA 0147861 (Canon KK), Nov. 17, 1981 (Abstract).

Derwent Publications Ltd., London, J,A, 0143273 (Canon KK), Nov. 7, 1981. (Abstract).

Abstract of Patent, JA 0143272 (Canon KK), Nov. 7, 1981 (Abstract).

Abstract of Patent, JA 0136861 (Canon KK), Oct. 26, 1981 (Abstract).

Abstract of Patent, JA 6133378 (Canon KK), Oct. 19, 1981 (Abstract).

Abstract of Patent, JA 6133377 (Canon KK), Oct. 19, 1981 (Abstract).

Abstract of Patent, JA 6093775 (Canon KK), Jul. 29, 1981 (Abstract).

Derwent Publications Ltd., London, J,A, 008135 (Ricoh KK), Jan. 27, 1981. (Abstract).

Derwent Publications Ltd., London, J,A, 0004488 (Canon KK), Jan. 17, 1981. (Abstract).

Abstract of Patent, JA 0004488 (Canon KK), Jan. 17, 1981 (Abstract).

Kirk–Othmer "Metallic Coatings," *Encyclopedia of Chemical Technology* 15 241–274 1981.

Komiyama et al. "One–Pot Preparation of 4–Hydroxychalcone β–Cyclodextrin as Catalyst," *Makromol. Chem.* 2 733–734 1981.

Derwent Publications, Ltd., London CA 1086–719 (Sherwood Medical) Sep. 30, 1980 (abstract).

Rosanske et al. "Stoichiometric Model of Cyclodextrin Complex Formation" *Journal of Pharmaceutical Sciences* 69 (5) 564–567 1980.

Semple et al. "Synthesis of Functionalized Tetrahydrofurans," *Tetrahedron Letters* 81 pp. 4561–4564 1980.

Kirk–Othmer "Film Deposition Techniques," *Encyclopedia of Chemical Technology* 10 247–283 1980.

Derwent World Patents Index, Derwent Info. Ltd., JP 54158941 (Toyo Pulp KK), Dec. 15, 1979. (Abstract).

Derwent World Patents Index, JP 54117536 (Kawashima F) Sep. 12, 1979.

Derwent Publications Ltd., London, J,A, 0005422 (Fuji Photo Film KK), Jan. 16, 1979. (Abstract).

Drexhage et al. "Photo–bleachable dyes and processes" *Research Disclosure* 85–87 1979.

"Color imaging devices and color filter arrays using photo–bleachable dyes" *Research Disclosure* 22–23 1979.

Wolff, N.E., et al. "Electrophotography" *Kirk–Othmer Encyclopedia of Chemical Technology* 8 794–826 1979.

Derwent Publications Ltd., London, J,A, 0012037 (Pentel KK), Jan. 29, 1977. (Abstract).

Abstract of Patent, JA 0012037 (Pentel KK), Jan. 29, 1977 (Abstract).

Jenkins, P.W. et al. "Photobleachable dye material" *Research Disclosure* 18 [No. 12932] 1975.

Lamberts, R.L. "Recording color grid patterns with lenticules" *Research Disclosure* 18–19 [No. 12923] 1975.

Karmanova, L.S. et al. "Light stabilizers of daytime fluorescent paints" *Chemical Abstracts* 82 147 [No. 59971p] 1975.

Prokopovich, B. et al. "Selection of effective photoinducers for rapid hardening of polyester varnish PE–250" *Chemical Abstracts* 83 131 [No. 81334a] 1975.

"Variable Contrast Printing System" *Research Disclosure* 19 [No. 12931] 1975.

Lakshman "Electronic Absorption Spectrum of Copper Formate Tetrahydrate" *Chemical Physics Letters* 31 (2) 331–334 1975.

Derwent Publications, Ltd., London J4 9131–226 (TNational Cash Register C) Dec. 16, 1974 (abstract).

Chang, I.F., et al. "Color Modulated Dye Ink Jet Printer" *IBM Technical Disclosure Bulletin* 17(5) 1520–1521 1974.

"Darocur 1173: Liquid Photoiniator for Ultraviolet Curing of Coatings" 1974.

Hosokawa et al. "Ascofuranone, an antibiotic from Ascochyta," Japan Kokai 73 91,278 (Nov. 28, 1973) *Merck Index* 80 p. 283; abstract 94259t 1974.

Abstract of patent, NL 7112489 (Dec. 27, 1971).

Gafney et al. "Photochemical Reactions of Copper (II)—1, 3–Diketonate Complexes" *Journal of the Americqal Chemical Society* 1971.

Derwent Publications, Ltd., London SU 292698–S Jan. 15, 1971 (abstract).

Derwent World Patents Index,CS 120380 (Kocourek, Jan) Oct. 15, 1966.

Ridgon, J.E. "In Search of Paper that Spies Can't Copy" *Wall Street Journal.*

Chatterjee,S. et al. "Photochemistry of Carbocyanine Alkyltriphenylborate Salts: Intra–Ion–Pair Electron Transfer and the Chemistry of Boranyl Radicals" *J. Am. Chem. Soc.* 112 6329–6338.

"Assay—Physical and Chemical Analysis of Complexes" AMAIZO.

"Cyclodextrin" AMAIZO.

"Beta Cyclodextrin Polymer (BCDP)" AMAIZO.

"Chemically Modified Cyclodextrins" AMAIZO.

"Cyclodextrin Complexation" American Maize Products Co.

"Monomers" Scientific Polymer Products Inc.

Suppan, Paul "Quenching of Excited States" *Chemistry and Light* 65–69.

Yamaguchi, H. et al. "Supersensitization. Aromatic ketones as supersensitizers" *Chemical Abstracts* 53 107 (d).

Stecher, H. "Ultraviolet–absorptive additives in adhesives, lacquers and plastics" *Chemical Abstracts* 53 14579 (c).

Maslennikov, A.S. "Coupling of diazonium salts with ketones" *Chemical Abstracts* 60 3128e.

Derwent Publications Ltd., London, 4 9128022.

Abstract of Patent, JP 405195450.

Rose, Philip I. "Gelatin," *Encyclopedia of Chemical Technology* 7 488–513.

Fig_2

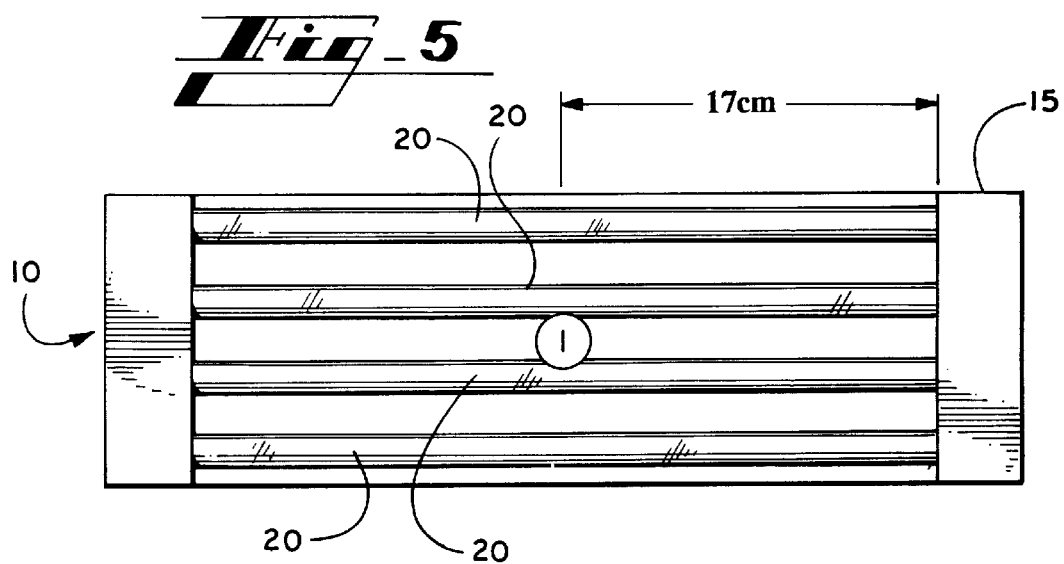
Fig_5

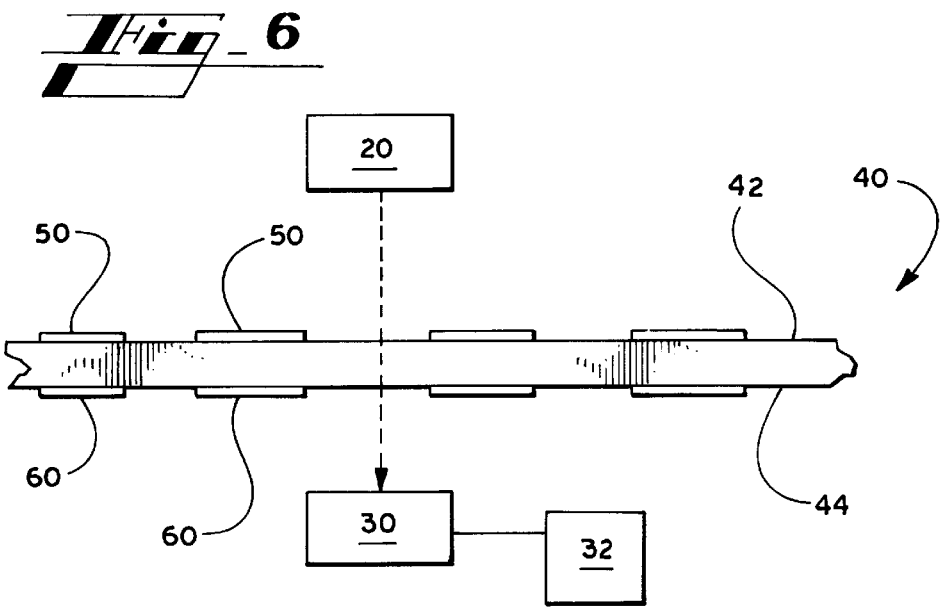
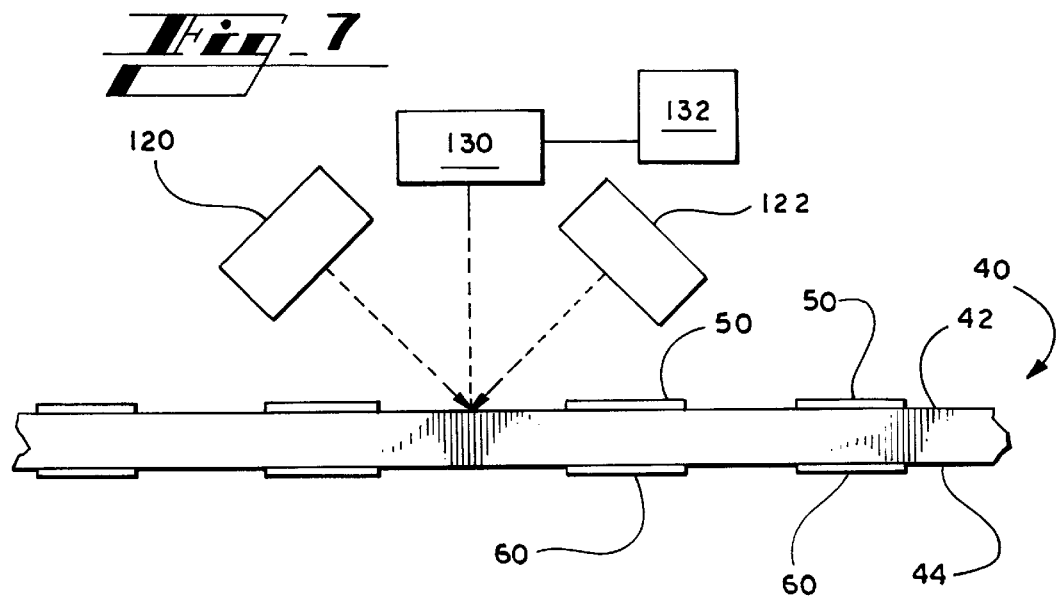

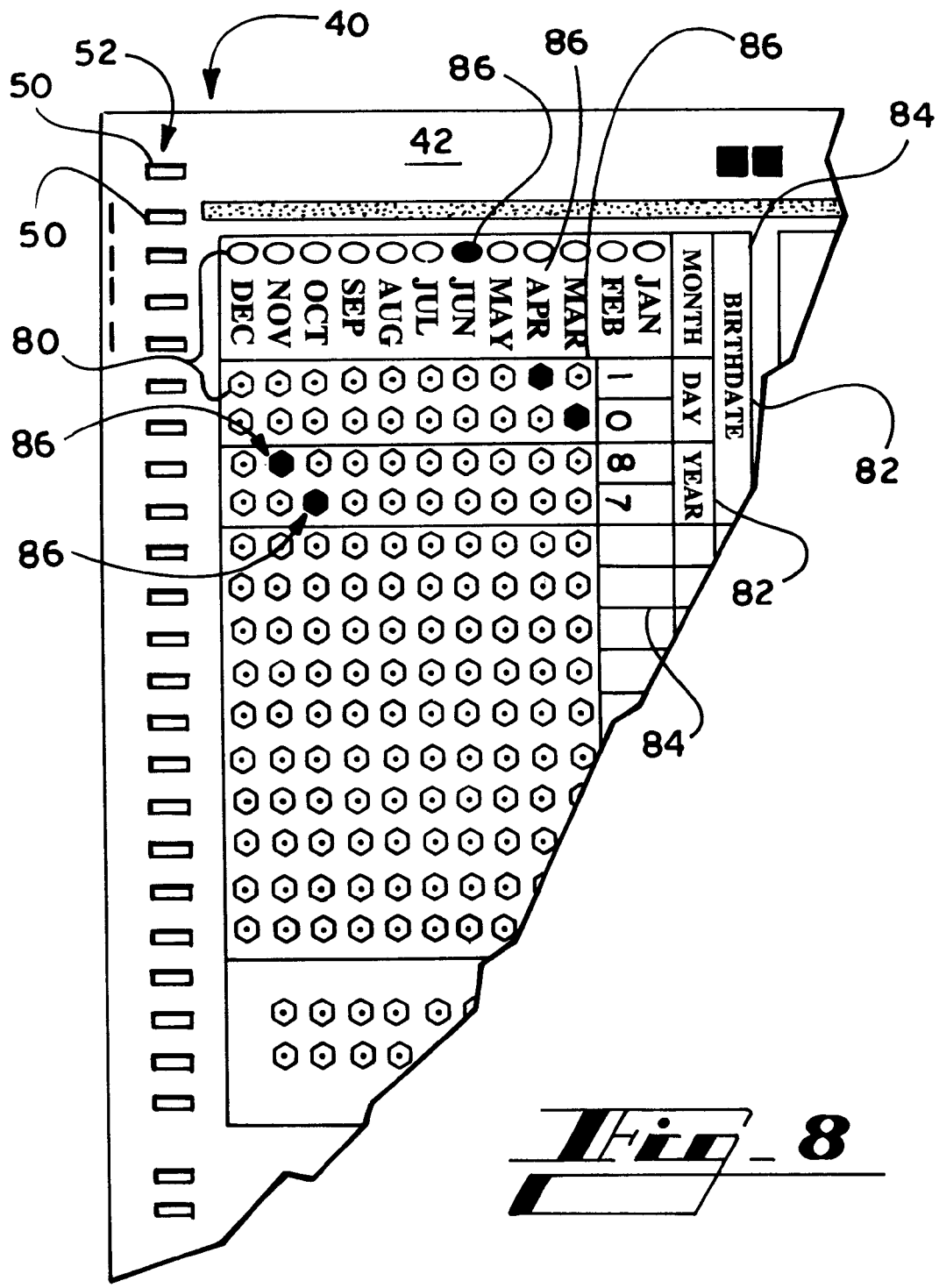
Fig_8

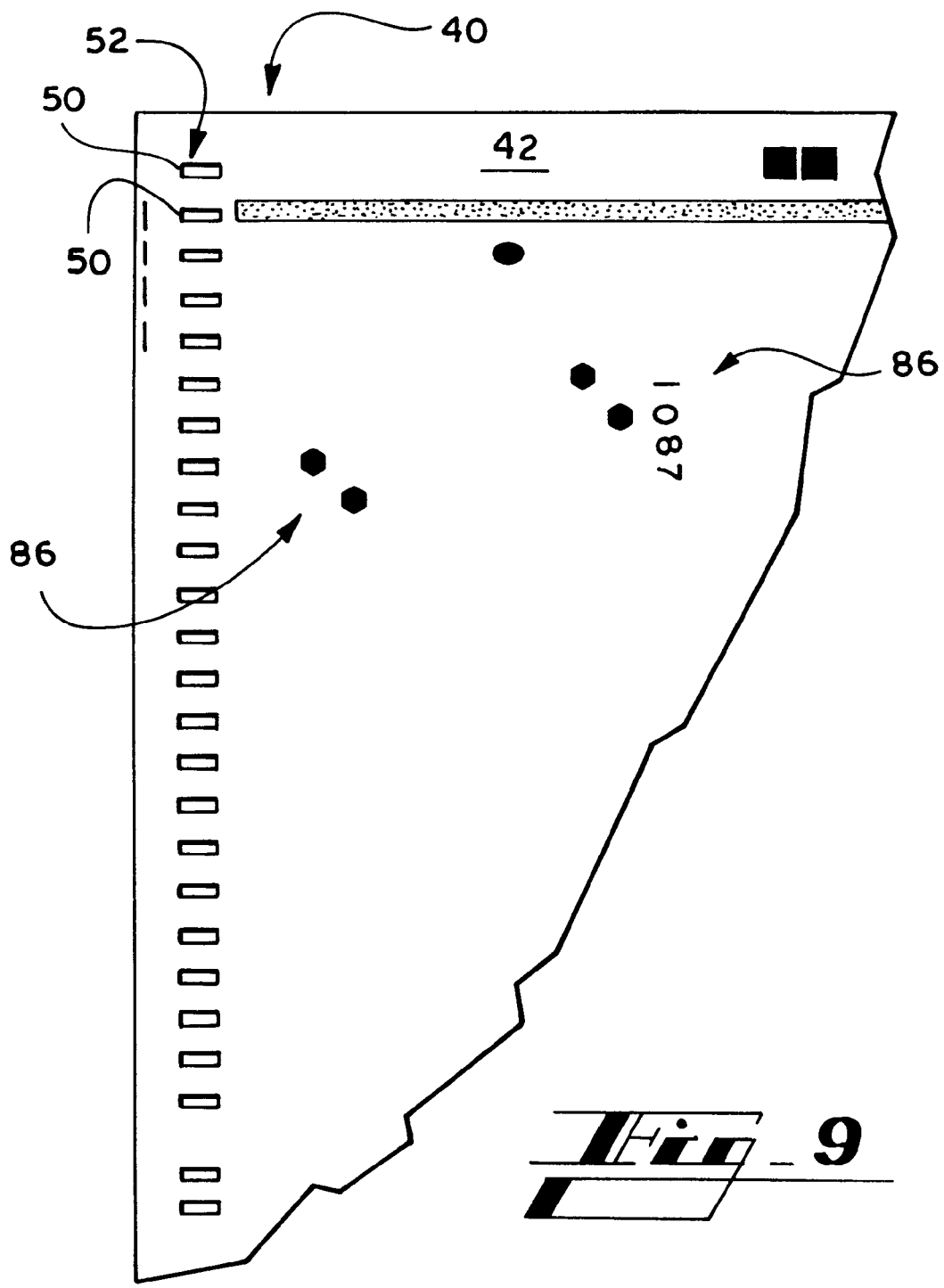

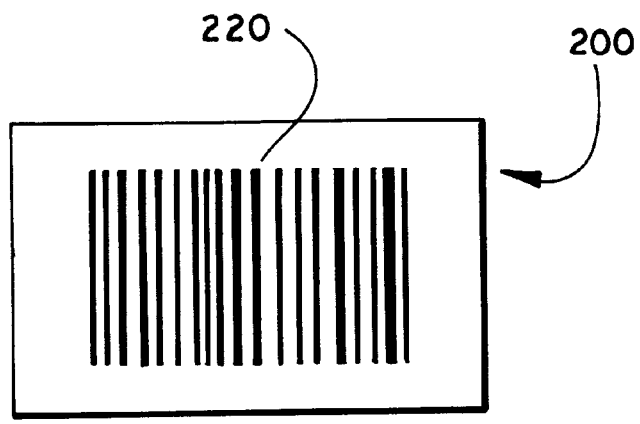
Fig_10
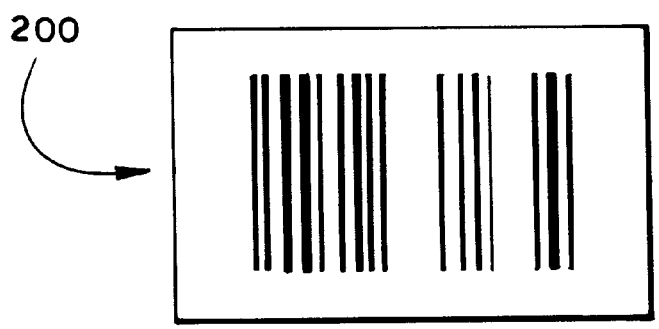
Fig_11

PHOTO-ERASABLE DATA PROCESSING FORMS AND METHODS

CROSS-REFERENCE TO RELATED APPLICATION

This is a continuation of U.S. application Ser. No. 08/777,996, filed Jan. 2, 1997, now U.S. Pat. No. 5,733,693, which is a continuation of U.S. application Ser. No. 08/453,912, filed May 30, 1995, now abandoned, which is a division of U.S. application Ser. No. 08/360,501, filed on Dec. 21, 1994, now U.S. Pat. No. 5,865,471, which is a continuation-in-part of U.S. application Ser. No. 08/258,858, filed on Jun. 13, 1994, now abandoned, which is a continuation-in-part of U.S. application Ser. No. 08/119,912, filed Sep. 10, 1993, now abandoned, and U.S. application Ser. No. 08/103,503, filed on Aug. 5, 1993 now abandoned.

TECHNICAL FIELD

The present invention relates generally to the field of optically scanned documents. More particularly, the present invention relates to a data processing document of the type used with photo-sensing apparatus that detect the presence of indicia at indicia-receiving locations on the document.

BACKGROUND OF THE INVENTION

Optical or conductive mark scanning systems of several types used to read and record large amounts of data very quickly are well known in the prior art. Such systems are typically used to process data from documents such as, for example, sheets of paper, cards, labels, tags, or other material. Generally speaking, some types of these documents have a plurality of pre-printed control marks (sometimes called "timing marks") in a control mark column (sometimes called a "timing track") used to trigger the system to scan or "read" certain data marks (also called "indicia") or data response areas (also called "indicia-receiving locations"). The data response areas are placed in a specified relation to the control marks. Usually, a firmware programmable read only memory (PROM) or software template and data processing means are used to keep track of control marks and data marks. The processing means will normally be programmed to work with a specific document format (e.g., it will expect a certain number of control marks and a certain pattern of data response areas in relation to the control marks).

At least two distinct optical scanning methods are used to detect the presence of indicia (e.g., data marks), control marks or other marks in data response areas (i.e., indicia-receiving locations). In one method, a light source placed at one surface of a document illuminates the area to be read and a photo-sensor placed at the opposite surface of the document is used to sense light that is transmitted through the document. The photo-sensor detects differences between the levels of light transmitted through marked and unmarked areas, in another method, both the light source and the photo-sensor are located on the same side of the document that is scanned. The photo-sensor detects differences between the levels of light reflected by marked and unmarked areas when they are illuminated. In both methods, the output of the photo-sensor is processed electronically to determine the presence or absence of a mark.

Both methods have limitations that may affect the ability of a photo-sensing apparatus to accurately detect the information on data processing forms. One limitation is related to the placement of indicia (e.g., data marks) in the data response areas (i.e., indicia-receiving locations). Each indicia-receiving location may be outlined or otherwise designated by some sort of marking printed on certain types of data processing forms. In some embodiments, indicia is placed in the indicia-receiving locations by darkening the designated area or by printing or writing a response in alpha-numeric characters or other such characters as may be required.

Inaccurate responses may be generated by the photo-sensing apparatus if the markings that designate the indicia-receiving location interfere with the proper detection of indicia. As an example, scannable answer sheets, census forms and the like are filled-out by providing indicia within designated indicia-receiving locations. If the indicia overlap any markings used to designate the indicia-receiving locations, they might be improperly read by the photo-sensor.

Conventional photo-sensing apparatus, which may incorporate computer software and/or hardware, are often configured to inspect or "look" precisely at areas designated to contain indicia and not at other areas in order to discriminate between indicia (e.g., data marks), stray indicia (e.g., stray data marks), non-indicia (e.g., material not intended to be detected by photo-sensing apparatus), smudges, flaws in the document, or the like. Moreover, data processing forms may have applications where only a few indicia-receiving locations are expected to contain indicia. In those situations, photo-sensing apparatus can be designed or programmed to ignore indicia sensed in other areas. It is important that the data processing form be as free of clutter or markings which may interfere with the processing in order to simplify the design of the photo-sensing apparatus and to enhance the accuracy of processing. Accordingly, it is very desirable to eliminate or otherwise render undetectable any text, graphics, position markers (e.g., marks defining indicia-receiving locations), or other markings that should not be detected by the photo-sensing apparatus prior to processing.

Another limitation of conventional data processing form relates to the indicia. In many situations, it may be desirable to quickly and efficiently erase or modify the indicia that are to be detected by photo-sensing apparatus. For example, data processing forms containing indicia (e.g., dots, shapes, alpha-numeric characters, lines, bars or the like) in formats, such as, for example, coupons, packaging labels, parts labels, bar code labels or tags, assembly-line work-in-progress labels or tags, or other items are used in such large numbers that the cost of reprinting or replacing the forms on each item simply to modify the indicia could become significant.

Accordingly, there is a need for a data processing form that can be used with a photo-sensing apparatus without the problem of indicia overlapping the markings used to designate indicia-receiving locations. There is also a need for a data processing form that permits quick and efficient erasure or modification of the indicia that are to be detected by photo-sensing apparatus.

SUMMARY OF THE INVENTION

The present invention addresses the needs described above by providing, in one embodiment, a data processing form for use with photo-sensing apparatus that detect the presence of indicia at indicia-receiving locations on the form. Generally speaking, the data processing form is composed of: 1) a sheet of carrier material; and 2) a plurality of indicia-receiving locations on at least a first surface of the sheet. The indicia-receiving locations are defined by a colored composition including a mutable colorant and an ultraviolet radiation transorber. When the colored composition is irradiated with ultraviolet radiation at a dosage level sufficient to irreversibly mutate the colorant, the indicia-receiving locations are adapted to become substantially undetectable by photo-sensing apparatus. Desirably, the colored composition is irradiated with radiation in the ultraviolet region of the electromagnetic spectrum having a wavelength range between approximately 100 to 375 nanometers.

The present invention also relates to a data processing form that includes a plurality of mutable indicia. At least a portion of the indicia are formed from a colored composition including a mutable colorant and an ultraviolet radiation transorber so that the indicia are adapted to become substantially undetectable by photo-sensing apparatus upon irradiation with an effective dosage level of ultraviolet radiation.

According to the invention, the data processing form may include text or graphics formed from the colored composition that includes a mutable colorant and an ultraviolet radiation transorber.

The data processing form may be configured in any conventional format. For example, the data processing form may be a transmitted-read form or a reflective-read form. The carrier material component of the data processing form may be substantially opaque, substantially translucent or substantially transparent.

The colored composition used in the data processing form of the present invention includes a colorant and an ultraviolet radiation transorber. The colorant, in the presence of the ultraviolet radiation transorber, is adapted, upon exposure of the transorber to ultraviolet radiation, to be mutable. The ultraviolet radiation transorber is adapted to absorb ultraviolet radiation and interact with the colorant to effect the irreversible mutation of the colorant. It is desirable that the ultraviolet radiation transorber absorb ultraviolet radiation at a wavelength of from about 4 to about 400 nanometers. It is even more desirable that the ultraviolet radiation transorber absorb ultraviolet radiation at a wavelength of 100 to 375 nanometers.

The colored composition which includes a colorant and an ultraviolet radiation transorber may also contain a molecular includant having a chemical structure which defines at least one cavity. The molecular includants include, but are not limited to, clathrates, zeolites, and cyclodextrins. Each of the colorant and ultraviolet radiation transorber is associated with one or more molecular includants. For example, the colorant may be at least partially included within a cavity of the molecular includant and the ultraviolet radiation transorber may be associated with the molecular includant outside of the cavity. As another example, the ultraviolet radiation transorber may be covalently coupled to the outside of the molecular includant.

The present invention encompasses a method for improving the readability of a data processing form used in photo-sensing apparatus. In general, the method includes the step of providing a data processing form that includes a sheet of carrier material and indicia located at a plurality of indicia-receiving locations on at least a first surface of the sheet. At least a portion of the indicia-receiving locations are defined by a mutable colored composition including a mutable colorant and an ultraviolet radiation transorber. Next, the colored composition is irradiated with ultraviolet radiation at a dosage level sufficient to irreversibly mutate the colorant so that the indicia-receiving locations are substantially undetectable by photo-sensing apparatus, leaving the indicia to be detected.

The present invention also encompasses a method of modifying indicia on a data processing form used in photo-sensing apparatus. In general, the method includes that step of providing a data processing form that includes a sheet of carrier material and a plurality of indicia at indicia-receiving locations on at least a first surface of the sheet. At least a portion of the indicia are mutable indicia formed from a colored composition comprising a mutable colorant and an ultraviolet radiation transorber. Next, the colored composition is irradiated with ultraviolet radiation at a dosage level sufficient to irreversibly mutate the colorant so that at least a portion of the mutable indicia are substantially undetectable by photo-sensing apparatus.

Desirably, the colored composition is irradiated with radiation in the ultraviolet region of the electromagnetic spectrum at a wavelength of from about 100 to about 375 nanometers. In some embodiments of the invention, it is desirable that the ultraviolet radiation is incoherent, pulsed ultraviolet radiation from a dielectric barrier discharge excimer lamp.

These and other objects, features and advantages of the present invention will become apparent after a review of the following detailed description of the disclosed embodiments and the appended claims.

BRIEF DESCRIPTION OF THE FIGURES

FIG. 5 is an illustration of several 222 nanometer excimer lamps arranged in four parallel columns wherein the location of the number "1" denotes the location where ten intensity measurements were obtained from increasing distances from the lamps at that location. (The measurements and their distances from the lamp are summarized in Table 7.)

FIG. 6 is an illustration of an exemplary photo-sensing apparatus based on the transmitted-read method.

FIG. 7 is an illustration of an exemplary photo-sensing apparatus based on the reflective-read method.

FIG. 8 is an illustration of a portion of an exemplary data processing form in which indicia-receiving locations are defined by a mutable colored composition.

FIG. 9 is an illustration of a portion of an exemplary data processing form depicted in FIG. 8 after the colorant in the mutable colored composition has been irreversibly mutated.

FIG. 10 is an illustration of an exemplary data processing form in which a portion of the indicia are formed from a mutable colored composition.

FIG. 11 is an illustration of an exemplary data processing form depicted in FIG. 10 after the colorant in the mutable colored composition has been irreversibly mutated.

DETAILED DESCRIPTION OF THE INVENTION

Figure 1:
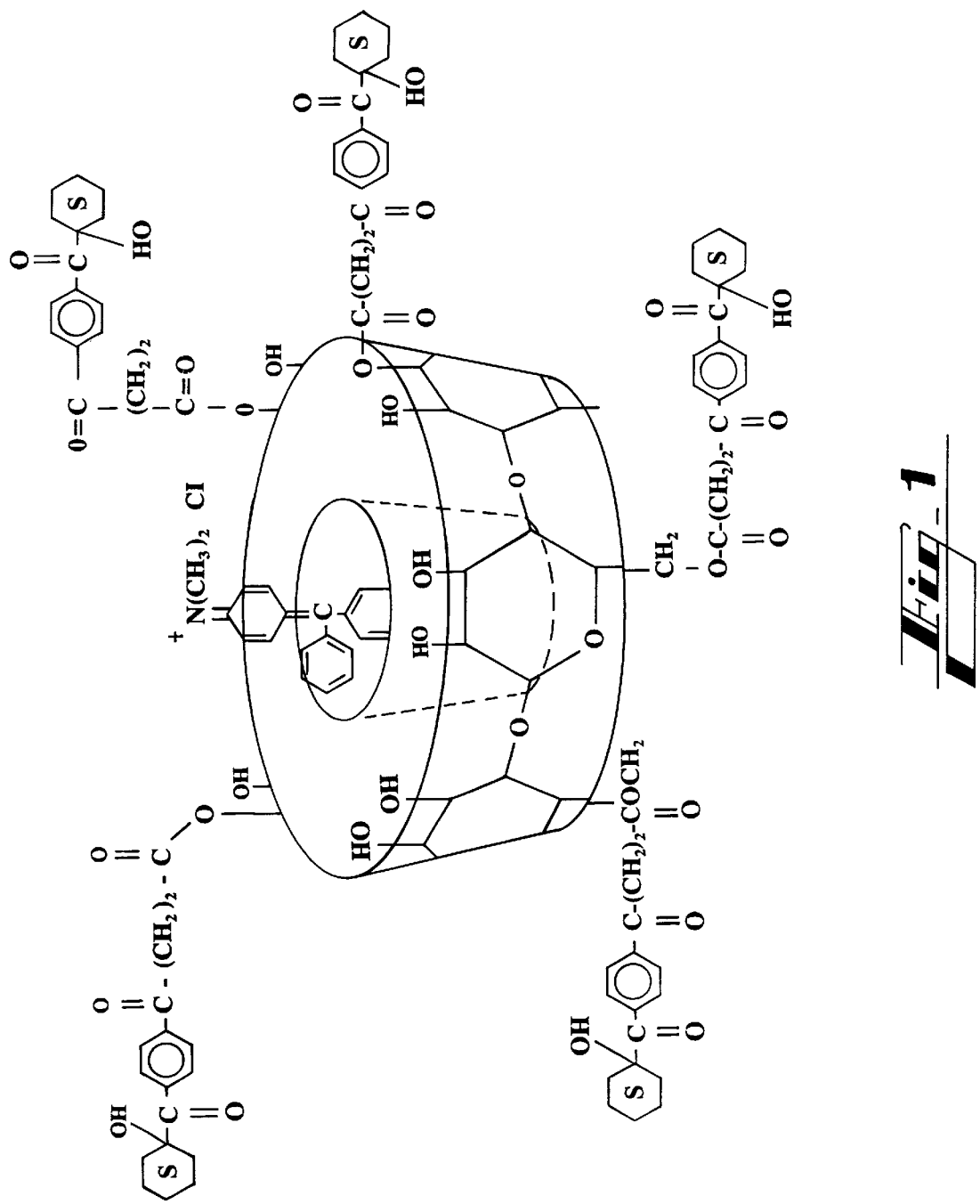
FIG. 1 illustrates an ultraviolet radiation transorber/mutable colorant/molecular includant complex wherein the mutable colorant is malachite green, the ultraviolet radiation transorber is IRGACURE® 184 (1-hydroxycyclohexyl phenyl ketone) and the molecular includant is β-cyclodextrin.

The present invention relates in general to a data processing form for use with photo-sensing apparatus that detect the presence of indicia at indicia-receiving locations on the form.

The term "data processing form" and such variations including "scannable form", "readable form", "scannable document" used herein refer to a document, sheet, label, card, tag, sticker or the like intended to hold information for detection by photo-sensing apparatus. A data processing form may exist as an individual object or it may be combined with or attached to items such as, for example, containers, vehicles, parts, inventory, equipment, packages and the like. Data processing forms can have many applications, including but not limited to, answer sheets, census forms, medical forms, identification cards, admission cards, admission tickets, credit cards, monetary instruments, checks, transportation tickets, coupons, bar code labels, bills, tags, or the like.

As used herein, the term "indicial" refers to markings such as, for example, dots, shapes, alpha-numeric characters, lines, bars or the like that have sufficient size, contrast and/or intensity to be detectable by photo-sensing apparatus.

As used herein, the term "indicia-receiving location" refers to a discrete area of a data processing form that defines a space where indicia may be placed for detection by photo-sensing apparatus. Such an area may be single, plural, ordered or patterned and can be referenced to control or reference marks used by a photo-sensing apparatus. Inks, dyes and/or other materials may be used to distinguish such an area from other areas of a data processing form.

As used herein, the term "photo-sensing apparatus" refers to conventional optical or conductive indicia (e.g., mark) scanning systems used to read data from data processing forms. Generally speaking, at least two distinct "photo-sensing" or optical scanning methods are used to detect the presence of indicia or other marks placed in response areas on data processing forms. In the transmitted-read method, a light source placed at one surface of a document illuminates an area to be read and a photo-sensor placed at the opposite surface of the document is used to sense light that is transmitted through the document at that area. When a mark is present, generally little or no light is transmitted through the document. In contrast, the absence of a mark means that significant light will pass through the document. The transmitted light is detected by the photo-sensor, and its output is processed by electrical circuitry to determine the presence or absence of a mark. Alternatively, and/or additionally, the wavelength or other characteristics of the light may be modified by transmission through indicia (e.g., marks) to create detectable differences. Exemplary transmitted-read methods are disclosed in U.S. Pat. No. 4,114,028. In the reflective-read method, both the light source and the photo-sensor are located on the same side of the document that is scanned. The photo-sensor receives reflected light when an area without a mark is illuminated. When a marked area is illuminated, the light sensor receives little or no reflected light. Again, the output of the photo-sensor is processed electronically to determine the presence or absence of a mark. Alternatively, and/or additionally, the wavelength or other characteristics of the light may be modified by reflecting off indica (e.g., marks) to create detectable differences. Systems using reflective-read methods are disclosed by U.S. Pat. Nos. 3,676,690 and 4,300,123.

As used herein, the term "substantially undetectable" refers to a state when indicia (or other markings such as, for example, outlines of indicia-receiving locations) on a data processing form that are detectable by a photo-sensing apparatus have been changed sufficiently so they fail to provide the same detectable response to transmitted or reflected light as unchanged indicia.

The term "composition" and such variations as "colored composition" which are used herein with reference to a data processing form refer to a colorant, and an ultraviolet radiation transorber. When reference is being made to a colored composition which is adapted for a specific application (e.g., a toner to be used in an electrophotographic process or a printing fluid to be used in a printing process employed in the preparation of the data processing forms), the term "composition-based" is used as a modifier to indicate that the material (e.g., a toner or a printing fluid) includes a colorant, an ultraviolet radiation transorber, and, optionally, a molecular includant.

As used herein, the term "colorant" is meant to include, without limitation, any material which, in the presence of an ultraviolet radiation transorber, is adapted upon exposure to ultraviolet radiation to be mutable. It is contemplated that radiation at wavelengths other than the ultraviolet region of the electromagnetic spectrum may be used to effect such mutation. The colorant typically will be an organic material, such as an organic dye or pigment, including toners and lakes. Desirably, the colorant will be substantially transparent to, i.e., will not significantly interact with, the ultraviolet radiation (or other effective wavelength of electromagnetic radiation) to which it is exposed. The term is meant to include a single material or a mixture of two or more materials.

Organic dye classes include, by way of illustration only, triaryl methyl dyes, such as Malachite Green Carbinol base {4-(dimethylamino)-α-[4-(dimethylamino)phenyl]-α-phenyl-benzene-methanol}, Malachite Green Carbinol hydrochloride {N-4-[[4-(dimethylamino)phenyl]-phenylmethylene]-2,5-cyclohexyldien-1-ylidene]-N-methyl-methanaminium chloride or bis [p-(dimethylamino)phenyl]phenylmethylium chloride}, and Malachite Green oxalate {N-4-[[4-(dimethylamino)phenyl]phenylmethylene]-2,5-cyclohexyldien-1-ylidene]-N-methylmethanaminium chloride or bis [p-(dimethylamino)phenyl]phenylmethylium oxalate}, Victoria Pure Blue BO {N-[4-[[4-diethylamino)phenyl]-[4-(ethylamino)-1-naphthalenyl]methylene]-2,5-cyclohexadien-1-yliden]-N-ethyl-ethanaminium chloride}, and Basic Fusion {4-[(4-aminophenyl)-(4-imino-2,5-cyclohexadien-1-ylidene)methyl]-benzenamine monohydrochloride}; monoazo dyes, such as Cyanine Black, Chrysoidine [Basic Orange 2; 4-(phenylazo)-1,3-benzenediamine monohydrochloride], and β-Naphthol Orange; thiazine dyes, such as Methylene Green, zinc chloride double salt [3,7-bis (dimethylamino)-6-nitrophenothiazin-5-ium chloride, zinc chloride double salt]; oxazine dyes, such as Lumichrome (7,8-dimethylalloxazine); naphthalimide dyes, such as Lucifer Yellow CH {6-amino-2-[(hydrazinocarbonyl)amino]-2,3-dihydro-1,3-dioxo-1H-benz[de]isoquinoline-5,8-disulfonic acid dilithium salt}; azine dyes, such as Janus Green B {3-(diethylamino)-7-[[4-(dimethylamino)phenyl]azo]-5-phenylphenazinium chloride}; cyanine dyes, such as Indocyanine Green {Cardio-Green or Fox Green; 2-[7-[1,3- dihydro-1,1-dimethyl-3-(4-sulfobutyl)-2H-benz [e]indol-2-ylidene]-1,3,5-heptatrienyl]-1,1-dimethyl-3-(4-sulfobutyl)-1H-benz [e] indolium hydroxide inner salt sodium salt}; indigo dyes, such as Indigo {Indigo Blue or Vat Blue 1; 2-(1,3-dihydro-3-oxo-2H-indol-2-ylidene)-1,2-dihydro-3H-indol-3-one}; coumarin dyes, such as 7-hydroxy-4-methylcoumarin (4-methylumbelliferone); benzimidazole dyes, such as Hoechst 33258 [bisbenzimide or 2-(4-hydroxyphenyl)-5-(4-methyl-1-pipera-zinyl)-2,5-bi-1H-benzimidazole trihydrochloride pentahydrate]; paraquincidal dyes, such as Hematoxylin {Natural Black 1; 7,11b-dihydrobenz [b]indeno [1,2-d]pyran-3,4,6a,9,10(6H)-pentol}; fluorescein dyes, such as Fluoresceinamine (5-aminofluorescein); diazonium salt dyes, such as Diazo Red RC (Azoic Diazo No. 10 or Fast Red RC salt; 2-methoxy-5-chlorobenzenediazonium chloride, zinc chloride double salt); azoic diazo dyes, such as Fast Blue BB salt (Azoic Diazo No. 20; 4-benzoylamino-2,5-diethoxybenzene diazonium chloride, zinc chloride double salt); phenylenediamine dyes, such as Disperse Yellow 9 [N-(2,4-dinitrophenyl)-1,4-phenylenediamine or Solvent Orange 53]; diazo dyes, such as Disperse Orange 13 [Solvent Orange 52; 1-phenylazo-4-(4-hydroxyphenylazo) naphthalene]; anthraquinone dyes, such as Disperse Blue 3 [Celliton Fast Blue FFR; 1-methylamino-4-(2-hydroxyethylamino)-9,10-anthraquinone], Disperse Blue 14 [Celliton Fast Blue B; 1,4-bis(methylamino)-9,10-anthraquinone], and Alizarin Blue Black B (Mordant Black 13); trisazo dyes, such as Direct Blue 71 {Benzo Light Blue FFL or Sirius Light Blue BRR; 3-[(4-[(4-[(6-amino-1-hydroxy-3-sulfo-2-naphthalenyl)azo]-6-sulfo-1-naphthalenyl)azo]-1-naphthalenyl)azo]-1,5-naphthalenedisulfonic acid tetrasodium salt}; xanthene dyes, such as 2,7-dichlorofluorescein; proflavine dyes, such as 3,6-diaminoacridine hemisulfate (Proflavine); sulfonaphthalein dyes, such as Cresol Red (o-cresolsulfonaphthalein); phthalocyanine dyes, such as Copper Phthalocyanine {Pigment Blue 15; (SP-4-1)-[29H,31H-phthalocyanato(2-)-$N^{29}$, $N^{31},N^{30}$, $N^{32}$]-copper}; carotenoid dyes, such as trans-$\beta$-carotene (Food Orange 5) ; carminic acid dyes, such as Carmine, the aluminum or calcium-aluminum lake of carminic acid (7-a-D-glucopyranosyl-9,10-dihydro-3,5,6,8-tetrahydroxy-1-methyl-9,10-dioxo-2-anthracenecarboxylic acid); azure dyes, such as Azure A [3-amino-7-(dimethylamino)phenothiazin-5-ium chloride or 7-(dimethylamino)-3-imino-3H-phenothiazine hydrochloride]; and acridine dyes, such as Acridine Orange [Basic Orange 14; 3,8-bis(dimethylamino)acridine hydrochloride, zinc chloride double salt] and Acriflavine (Acriflavine neutral; 3,6-diamino-10-methylacridinium chloride mixture with 3,6-acridinediamine).

The term "mutable" with reference to the colorant is used to mean that the absorption maximum of the colorant in the visible region of the electromagnetic spectrum is capable of being mutated or changed by exposure to ultraviolet radiation when in the presence of the ultraviolet radiation transorber. Alternatively and/or additionally, it is contemplated that radiation at wavelengths in other regions of the electromagnetic spectrum may be used. In general, it is only necessary that such absorption maximum be mutated to an absorption maximum which is different from that of the colorant prior to exposure to the ultraviolet radiation, and that the mutation be irreversible. Thus, the new absorption maximum can be within or outside of the visible region of the electromagnetic spectrum. In other words, the colorant can mutate to a different color or be rendered colorless, transparent, or otherwise substantially undetectable by conventional photo-sensing apparatus. The latter, of course, is desirable when the colorant is used in a colored composition adapted to be utilized in the data processing forms of the present invention.

As used herein, the term "irreversible" means that the colorant will not revert to its original color when it no longer is exposed to ultraviolet radiation (or radiation at other effective wavelengths in the electromagnetic radiation spectrum). Desirably, the mutated colorant will be stable, i.e., not appreciably adversely affected by radiation normally encountered in the environment, such as natural or artificial light and heat. Thus, desirably, a colorant rendered colorless, transparent, or otherwise substantially undetectable by conventional photo-sensing apparatus will remain colorless or substantially undetectable indefinitely.

The term "ultraviolet radiation transorber" is used herein to mean any material which is adapted to absorb ultraviolet radiation (or radiation at other effective wavelengths in the electromagnetic radiation spectrum) and interact with the colorant to effect the mutation of the colorant. In some embodiments, the ultraviolet radiation transorber may be an organic compound. The term "compound" is intended to include a single material or a mixture of two or more materials. If two or more materials are employed, it is not necessary that all of them absorb ultraviolet radiation of the same wavelength. It is contemplated that the transorber may be adapted to absorb radiation at other wavelengths The data processing form of the present invention incorporates a colored composition that includes unique compounds that are capable of absorbing narrow ultraviolet wavelength radiation (or radiation at other effective wavelengths in the electromagnetic radiation spectrum). The compounds are synthesized by combining a wavelength-selective sensitizer and a photoreactor. The photoreactors oftentimes do not efficiently absorb high energy radiation. When combined with wavelength-selective antennae that correspond to the eximer lamp emission, the resulting compound is a wavelength specific compound that efficiently absorbs a very narrow spectrum of radiation. Examples of ultraviolet radiation transorbers are shown in Examples 5 and 9 herein.

While the mechanism of the interaction of the ultraviolet radiation transorber with the colorant is not totally understood, it is believed that it may interact with the colorant in a variety of ways. For example, the ultraviolet radiation transorber, upon absorbing ultraviolet radiation, may be converted to one or more free radicals which interact with the colorant. Such free radical-generating compounds typically are hindered ketones, some examples of which include, but are not limited to: benzildimethyl ketal (available commercially as IRGACURE® 651, Ciba-Geigy Corporation, Hawthorne, N.Y.) ; 1-hydroxycyclohexyl phenyl ketone (IRGACURE® 500); 2-methyl-1-[4-(methylthio) phenyl]-2-morpholino-propan-1-one] (IRGACURE® 907); 2-benzyl-2-dimethylamino-1-(4-morpholinophenyl)butan-1-one (IRGACURE® 369); and 1-hydroxycyclohexyl phenyl ketone (IRGACURE® 184).

Alternatively, the ultraviolet radiation may initiate an electron transfer or reduction-oxidation reaction between the ultraviolet radiation transorber and the colorant. In this case, the ultraviolet radiation transorber may be, but is not limited to, Michler's ketone (p-dimethylaminophenyl ketone) or benzyl trimethyl stannate. Or, a cationic mechanism may be involved, in which case the ultraviolet radiation transorber could be, for example, bis[4-(diphenylsulphonio)phenyl)] sulfide bis-(hexafluorophosphate) (DEGACURE® KI85, Ciba-Geigy Corporation, Hawthorne, N.Y.) ; CYRA-CURE® UVI-6990 (Ciba-Geigy Corporation), which is a mixture of bis[4-(diphenylsulphonio)phenyl] sulfide bis (hexafluorophosphate) with related monosulphonium hexafluorophosphate salts; and 5-2,4-(cyclopentadienyl) [1,2,3,4,5,6-(methylethyl)benzene]-iron-(II) hexafluorophosphate (IRGACURE® 261).

The term "ultraviolet radiation" is used herein to mean electromagnetic radiation having wavelengths in the range of from about 4 to about 400 nanometers. An especially desirable ultraviolet radiation wavelength range is between approximately 100 to 375 nanometers. Thus, the term includes the regions commonly referred to as ultraviolet and vacuum ultraviolet. The wavelength ranges typically assigned to these two regions are from about 180 to about 400 nanometers and from about 100 to about 180 nanometers, respectively.

In some embodiments, the molar ratio of ultraviolet radiation transorber to colorant generally will be equal to or greater than about 0.5. As a general rule, the more efficient the ultraviolet radiation transorber is in absorbing the ultraviolet radiation and interacting with, i.e., transferring absorbed energy to, the colorant to effect irreversible mutation of the colorant, the lower such ratio can be. Current theories of molecular photo chemistry suggest that the lower limit to such ratio is 0.5, based on the generation of two free radicals per photon. As a practical matter, however, ratios higher than 1 are likely to be required, perhaps as high as about 10. However, the colored compositions used with the data processing form of the present invention are not bound by any specific molar ratio range. The important feature is that the transorber is present in an amount sufficient to effect mutation of the colorant.

As a practical matter, the colorant, and ultraviolet radiation transorber are likely to be solids. However, any or all of such materials can be a liquid. In an embodiment where the colored composition is a solid, the effectiveness of the ultraviolet radiation transorber is improved when the colorant and ultraviolet radiation transorber are in intimate contact. To this end, the thorough blending of the two components, along with other components which may be present, is desirable. Such blending generally is accomplished by any of the means known to those having ordinary skill in the art. When the colored composition includes a polymer, blending is facilitated if the colorant and the ultraviolet radiation transorber are at least partly soluble in softened or molten polymer. In such case, the composition is readily prepared in, for example, a two-roll mill. Alternatively, the colored composition can be a liquid because one or more of its components is a liquid.

For some applications, the colored composition typically will be utilized in particulate form. In other applications, the particles of the composition should be very small. For example, the particles of a colored composition adapted for use as a toner in an electrophotdgraphic process that can be used to prepare the data processing forms of the present invention may typically consist of 7–15 micrometer average diameter particles, although smaller or larger particles can be employed. In such an application, the particles should be as uniform in size as possible. Methods of forming such particles are well known to those having ordinary skill in the art.

Photochemical processes involve the absorption of light quanta, or photons, by a molecule, e.g., the ultraviolet radiation transorber, to produce a highly reactive electronically excited state. However, the photon energy, which is proportional to the wavelength of the radiation, cannot be absorbed by the molecule unless it matches the energy difference between the unexcited, or original, state and an excited state. Consequently, while the wavelength range of the ultraviolet radiation to which the colored composition is exposed is not directly of concern, at least a portion of the radiation must have wavelengths which will provide the necessary energy to raise the ultraviolet radiation transorber to an energy level which is capable of interacting with the colorant.

It follows, then, that the absorption maximum of the ultraviolet radiation transorber ideally will be matched with the wavelength range of the ultraviolet radiation in order to increase the efficiency of the mutation of the colorant. Such efficiency also will be increased if the wavelength range of the ultraviolet radiation is relatively narrow, with the maximum of the ultraviolet radiation transorber coming within such range. For these reasons, especially suitable ultraviolet radiation has a wavelength of from about 100 to about 375 nanometers. Ultraviolet radiation within this range desirably may be incoherent, pulsed ultraviolet radiation from a dielectric barrier discharge excimer lamp.

The term "incoherent, pulsed ultraviolet radiation" has reference to the radiation produced by a dielectric barrier discharge excimer lamp (referred to hereinafter as "excimer lamp"). Such a lamp is described, for example, by U. Kogelschatz, "Silent discharges for the generation of ultraviolet and vacuum ultraviolet excimer radiation," *Pure & Appl. Chem.*, 62, No. 9, pp. 1667–1674 (1990); and E. Eliasson and U. Kogelschatz, "UV Excimer Radiation from Dielectric-Barrier Discharges," *Appl. Phys. B*, 46, pp. 299–303 (1988). Excimer lamps were developed originally by ABB Infocom Ltd., Lenzburg, Switzerland. The excimer lamp technology since has been acquired by Haraus Noblelight AG, Hanau, Germany.

The excimer lamp emits radiation having a very narrow bandwidth, i.e., radiation in which the half width is of the order of 5–15 nanometers. This emitted radiation is incoherent and pulsed, the frequency of the pulses being dependent upon the frequency of the alternating current power supply which typically is in the range of from about 20 to about 300 kHz. An excimer lamp typically is identified or referred to by the wavelength at which the maximum intensity of the radiation occurs, which convention is followed throughout this specification. Thus, in comparison with most other commercially useful sources of ultraviolet radiation which typically emit over the entire ultraviolet spectrum and even into the visible region, excimer lamp radiation is substantially monochromatic.

Excimers are unstable molecular complexes which occur only under extreme conditions, such as those temporarily existing in special types of gas discharge. Typical examples are the molecular bonds between two rare gaseous atoms or between a rare gas atom and a halogen atom. Excimer complexes dissociate within less than a microsecond and, while they are dissociating, release their binding energy in the form of ultraviolet radiation. Known excimers, in general, emit in the range of from about 125 to about 360 nanometers, depending upon the excimer gas mixture.

Although the colorant and the ultraviolet radiation transorber have been described as separate compounds, they can be part of the same molecule. For example, they can be covalently coupled to each other, either directly, or indirectly through a relatively small molecule, or spacer. Alternatively, the colorant and ultraviolet radiation transorber can be covalently coupled to a large molecule, such as an oligomer or a polymer, particularly when a solid colored composition is desired. Further, the colorant and ultraviolet radiation transorber may be associated with a large molecule by van der Waals forces, and hydrogen bonding, among other means. Other variations will be readily apparent to those having ordinary skill in the art.

For example, the colored composition may also contain a molecular includant. The term "molecular includant," as used herein, is intended to mean any substance having a chemical structure which defines at least one cavity. That is, the molecular includant is a cavity-containing structure. As used herein, the term "cavity" is meant to include any opening or space of a size sufficient to accept at least a portion of one or both of the colorant and the ultraviolet radiation transorber. Thus, the cavity can be a tunnel through the molecular includant or a cave-like space in the molecular includant. The cavity can be isolated or independent, or connected to one or more other cavities.

The molecular includant can be inorganic or organic in nature. In certain embodiments, the chemical structure of the molecular includant is adapted to form a molecular inclusion complex. Examples of molecular includants are, by way of illustration only, clathrates or intercalates, zeolites, and cyclodextrins. Examples of cyclodextrins include, but are not limited to, alpha-cyclodextrin, beta-cyclodextrin, gamma-cyclodextrin, hydroxypropyl beta-cyclodextrin, hydroxyethyl beta-cyclodextrin, sulfated beta-cyclodextrin, and sulfated gamma-cyclodextrin. (American Maize-Products Company, of Hammond Ind.) In some embodiments, the molecular includant is a cyclodextrin. More particularly, in some embodiments, the molecular includant is an alpha-cyclodextrin. In other embodiments, the molecular includant is a beta-cyclodextrin. Although not wanting to be bound by the following theory, it is believed that the closer the transorber molecule is to the mutable colorant on the molecular includant, the more efficient the interaction with the colorant to effect mutation of the colorant. Thus, the molecular includant with functional groups that can react with and bind the transorber molecule and that are close to the binding site of the mutable colorant are the more desirable molecular includants.

As used herein, the term "derivatized molecular includant" is used herein to mean a molecular includant having more than two leaving groups covalently coupled to each molecule of the molecular includant. The term "leaving group" is used herein to mean any leaving group capable of participating in a bimolecular nucleophilic substitution reaction.

The colorant and the ultraviolet radiation transorber are associated with the molecular includant. The term "associated" in its broadest sense means that the colorant and the ultraviolet radiation transorber are at least in close proximity to the molecular includant. For example, the colorant and/or the ultraviolet radiation transorber can be maintained in close proximity to the molecular includant by hydrogen bonding, van der Waals forces, or the like. Alternatively, either or both of the colorant and the ultraviolet radiation transorber can be covalently bonded to the molecular includant. In certain embodiments, the colorant will be associated with the molecular includant by means of hydrogen bonding and/or van der Waals forces or the like, while the ultraviolet radiation transorber is covalently bonded to the molecular includant. In other embodiments, the colorant is at least partially included within the cavity of the molecular includant, and the ultraviolet radiation transorber is located outside of the cavity of the molecular includant. In one embodiment wherein the colorant and the ultraviolet radiation transorber are associated with the molecular includant, the colorant is crystal violet, the ultraviolet radiation transorber is a dehydrated phthaloylglycine-2959, and the molecular includant is beta-cyclodextrin. In yet another embodiment wherein the colorant and the ultraviolet radiation transorber are associated with the molecular includant, the colorant is crystal violet, the ultraviolet radiation transorber is 4(4-hydroxyphenyl) butan-2-one-2959 (chloro substituted), and the molecular includant is beta-cyclodextrin.

Figure 2:
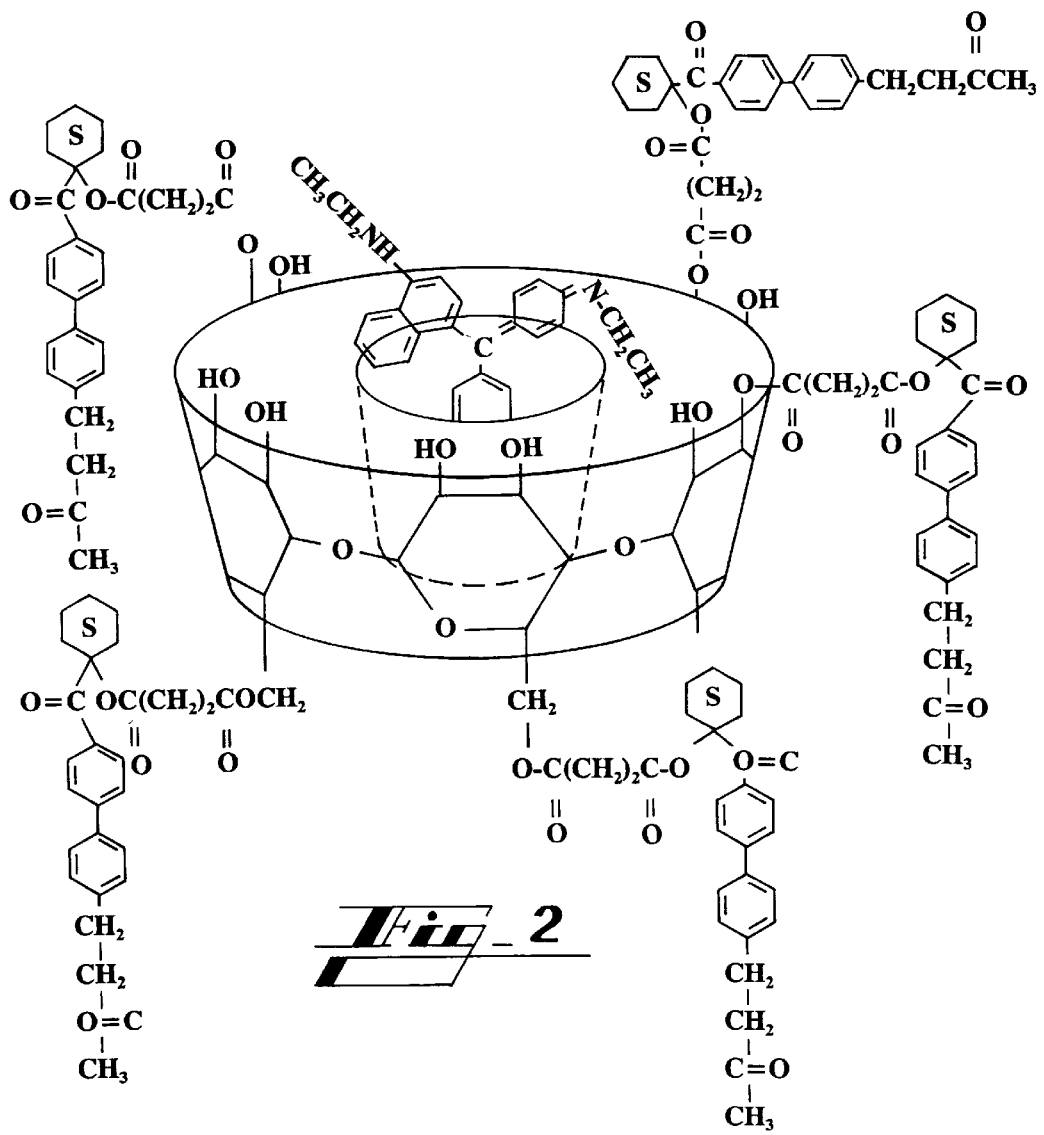
FIG. 2 illustrates an ultraviolet radiation transorber/mutable colorant/molecular includant complex wherein the mutable colorant is victoria pure blue BO (Basic Blue 7), the ultraviolet radiation transorber is IRGACURE® 184 (1-hydroxycyclohexyl phenyl ketone), and the molecular includant is β-cyclodextrin.

In another embodiment wherein the colorant and the ultraviolet radiation transorber are associated with the molecular includant, the colorant is malachite green, the ultraviolet radiation transorber is IRGACURE® 184, and the molecular includant is beta-cyclodextrin as shown in FIG. 1. In still another embodiment wherein the colorant and the ultraviolet radiation transorber are associated with the molecular includant, the colorant is victoria pure blue BO, the ultraviolet radiation transorber is IRGACURE® 184, and the molecular includant is beta-cyclodextrin as shown in FIG. 2.

Examples 5 through 9 disclose a method of preparing and associating these colorants and ultraviolet radiation transorbers to beta-cyclodextrins. It is to be understood that the methods disclosed in Examples 5 through 9 are merely one way of preparing and associating these components, and that many other methods known in the chemical arts may be used. Other methods of preparing and associated such components, or any of the other components which may be used in the colored composition would be known to those of ordinary skill in the art once the specific components have been selected.

As a practical matter, the colorant, ultraviolet radiation transorber, and molecular includant are likely to be solids. However, any or all of such materials can be a liquid. The colored composition can be a liquid either because one or more of its components is a liquid, or, when the molecular includant is organic in nature, a solvent is employed. Suitable solvents include, but are not limited to, amides, such as N,N-dimethylformamide; sulfoxides, such as dimethylsulfoxide; ketones, such as acetone, methyl ethyl ketone, and methyl butyl ketone; aliphatic and aromatic hydrocarbons, such as hexane, octane, benzene, toluene, and the xylenes; esters, such as ethyl acetate; water; and the like. When the molecular includant is a cyclodextrin, particularly suitable solvents are the amides and sulfoxides.

The present invention also relates to a method of mutating the colorant in the colored composition employed in the data processing forms of the present invention. Briefly described, the method includes the step of irradiating a composition containing a mutable colorant and an ultraviolet radiation transorber with ultraviolet radiation at a dosage level sufficient to mutate the colorant. As stated above, the composition may include a molecular includant.

The amount or dosage level of ultraviolet radiation that the colorant is exposed to will generally be that amount which is necessary to mutate the colorant. The amount of ultraviolet radiation necessary to mutate the colorant can be determined by one of ordinary skill in the art using routine experimentation. Power density is the measure of the amount of radiated electromagnetic power traversing a unit area and is usually expressed in watts per centimeter squared (W/cm$^2$). The power density level range is between approximately 5 mW/cm$^2$ and 15 mw/cm$^2$, more particularly 8 to 10 mW/cm$^2$. The dosage level, in turn, typically is a function of the time of exposure and the intensity or flux of the radiation source which irradiates the colored composition. The latter is effected by the distance of the composition from the source and, depending upon the wavelength range of the ultraviolet radiation, can be effected by the atmosphere between the radiation source and the composition. Accordingly, in some instances it may be appropriate to expose the composition to the radiation in a controlled atmosphere or in a vacuum, although in general neither approach is desired.

Figure 3:
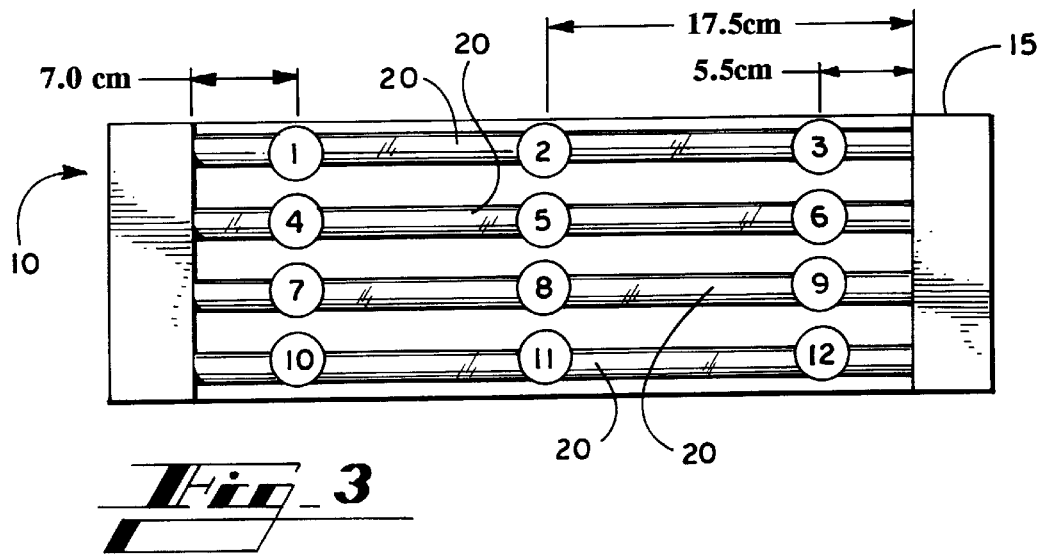
FIG. 3 is an illustration of several 222 nanometer excimer lamps arranged in four parallel columns wherein the twelve numbers represent the locations where twelve intensity measurements were obtained approximately 5.5 centimeters from the excimer lamps.
Figure 4:
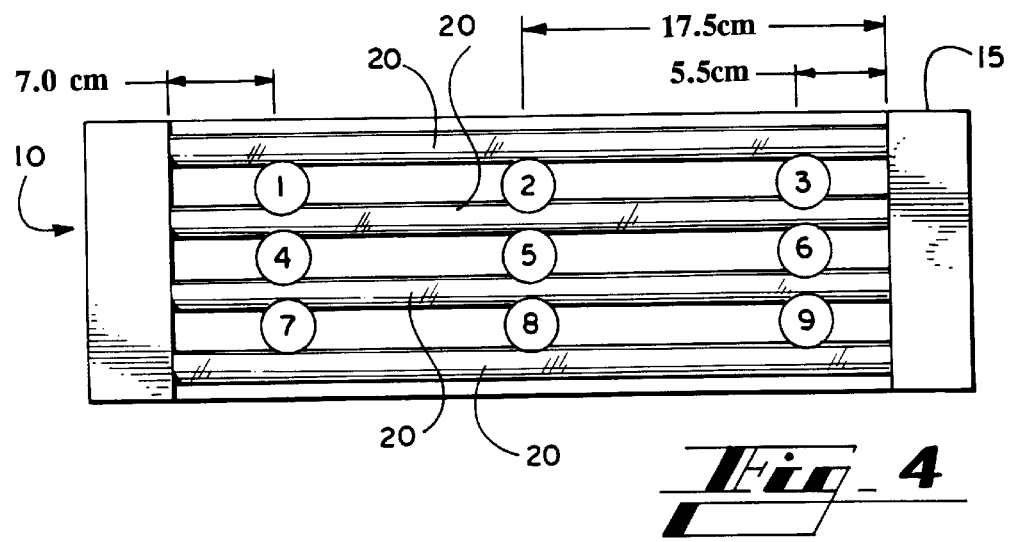
FIG. 4 is an illustration of several 222 nanometer excimer lamps arranged in four parallel columns wherein the nine numbers represent the locations where nine intensity measurements were obtained approximately 5.5 centimeters from the excimer lamps.

For example, in one embodiment, the colorant is mutated by exposure to 222 nanometer excimer lamps. More particularly, the colorant crystal violet is mutated by exposure to 222 nanometer lamps. Even more particularly, the colorant crystal violet is mutated by exposure to 222 nanometer excimer lamps located approximately 5 to 6 centimeters from the colorant, wherein the lamps are arranged in four parallel columns approximately 30 centimeters long as shown in FIGS. 3 and 4. It is to be understood that the arrangement of the lamps is not critical to this aspect of the invention. Accordingly, one or more lamps may be arranged in any configuration and at any distance which results in the colorant mutating upon exposure to the lamp's ultraviolet radiation. One of ordinary skill in the art would be able to determine by routine experimentation which configurations and which distances are appropriate. Also, it is to be understood that different excimer lamps are to be used with different ultraviolet radiation transorbers. The excimer lamp used to mutate a colorant associated with an ultraviolet radiation transorber should produce ultraviolet radiation of a wavelength that is absorbed by the ultraviolet radiation transorber.

The colored composition can be utilized on or in any sheet of carrier material (i.e., substrate) used to make the data processing form. It is important only that the colored composition form a plurality of indicia or define a plurality of indicia-receiving locations which generally appear to be "at about" or on at least a first surface of the sheet. Accordingly, the expression "a plurality of indicia-receiving locations on at least a surface of the sheet" should be understood to encompass a plurality of indicia-receiving locations which generally appear to be "at about" or on at least a first surface of the sheet. Likewise, the expression "a plurality of indicia at indicia-receiving locations on at least a surface of the sheet" should be understood to encompass a plurality of indicia at indicia-receiving locations, both of which generally appear to be "at about" or on at least a first surface of the sheet.

If the composition is present in the sheet of carrier material, however, the carrier material should be substantially transparent to the ultraviolet radiation which is employed to mutate the colorant. That is, the ultraviolet radiation (or radiation at other effective wavelengths in the electromagnetic radiation spectrum) will not significantly interact with or be absorbed by the carrier material. As a practical matter, the composition typically will be placed on or incorporated into a sheet of carrier material, with the most common carrier material being paper. Other carrier materials, including, but not limited to, woven and non-woven webs or fabrics, films, cards, cardboard, or the like, can be used. It is contemplated that the composition may be placed directly on other items to be processed by photosensing apparatus, including but not limited to, packaging, inventory, products, equipment, machinery, parts, vehicles, collars, tags, containers, or the like.

The data processing form of the present invention contains indicia-receiving locations defined by the mutable colored composition described herein. Alternatively and/or additionally, the data processing form of the present invention may contain indicia, text and/or graphics formed from the mutable colored composition described herein. Although the data processing form of the present invention may employ any sheet of carrier material capable of having the colored composition fixed thereto or incorporated therein, a desirable carrier material is paper. Particular examples include, but are not limited to, photocopy paper and facsimile paper.

By way of example, the colored composition can be incorporated into a toner adapted to be utilized in an electrophotographic process employed in the production of the data processing forms. The toner includes the colorant, ultraviolet radiation transorber, and a vehicle. The vehicle can be a polymer, and the toner may further contain a charge control agent. Briefly described, the electrophotographic process comprises the steps of creating an image on a photoreceptor surface, applying toner to the photoreceptor surface to form a toner image which replicates the image, transferring the toner image to a substrate, and fixing the toner image to the substrate. After the toner has been fixed on the substrate, the colorant in the composition is mutated by irradiating the substrate with ultraviolet radiation at a dosage level sufficient to irreversibly mutate the colorant. In some embodiments, the ultraviolet radiation used to mutate the colorant will have wavelengths of from about 100 to about 375 nanometers. In other embodiments, the ultraviolet radiation is incoherent, pulsed ultraviolet radiation produced by a dielectric barrier discharge excimer lamp. In another embodiment, the toner may further comprise a molecular includant.

When the colored composition is adapted to be utilized as a toner in an electrophotographic process (in the manufacture of the data processing forms of the present invention), the composition also will contain a vehicle, the nature of which is well known to those having ordinary skill in the art. For many applications, the carrier will be a polymer, typically a thermosetting or thermoplastic polymer, with the latter being the more common.

Further examples of thermoplastic polymers include, but are not limited to: end-capped polyacetals, such as poly (oxymethylene) or polyformaldehyde, poly (trichloroacetaldehyde), poly(n-valeraldehyde), poly (acetaldehyde), poly(propionaldehyde), and the like; acrylic polymers, such as polyacrylamide, poly(acrylic acid), poly (methacrylic acid), poly(ethyl acrylate), poly(methyl methacrylate), and the like; fluorocarbon polymers, such as poly(tetrafluoroethylene), perfluorinated ethylenepropylene copolymers, ethylenetetrafluoroethylene copolymers, poly-(chlorotrifluoroethylene), ethylene-chlorotrifluoroethylene copolymers, poly(vinylidene fluoride), poly(vinyl fluoride), and the like; epoxy resins, such as the condensation products of epichlorohydrin and bisphenol A; polyamides, such as poly(6-aminocaproic acid) or poly(E-caprolactam), poly (hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene),poly (sulfonyl-1,4-phenyleneoxy-1,4-phenylenesulfonyl-4,4-biphenylene), and the like; polycarbonates, such as poly (bisphenol A) or poly(carbonyldioxy-1,4- phenyleneisopropylidene-1,4-phenylene) and the like; polyesters, such as poly(ethylene terephthalate) poly (tetramethylene terephthalate), poly(cyclohexylene-1,4-dimethylene terephthalate) or poly(oxymethylene-1,4-cyclohexylenemethyleneoxyterephthaloyl), and the like; polyaryl sulfides, such as poly(p-phenylene sulfide) or poly (thio-1,4-phenylene), and the like; polyimides, such as poly-(pyromellitimido-1,4-phenylene), and the like; polyolefins, such as polyethylene, polypropylene, poly(1-butene), poly (2-butene), poly(1-pentene) poly(2-pentene) poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly (vinylidene chloride), polystyrene, and the like; and copolymers of the foregoing, such as acrylonitrile-butadienestyrene (ABS) copolymers, styrene-n-butylmethacrylate copolymers, ethylenevinyl acetate copolymers, and the like.

Some of the more commonly used thermoplastic polymers include styrene-n-butyl methacrylate copolymers, polystyrene, styrene-n-butyl acrylate copolymers, styrene-butadiene copolymers, polycarbonates, poly(methyl methacrylate), poly(vinylidene fluoride), polyamides (nylon-12), polyethylene, polypropylene, ethylene-vinyl acetate copolymers, and epoxy resins.

Examples of thermosetting polymers include, but are not limited to, alkyd resins, such as phthalic anhydride-glycerol resins, maleic acid-glycerol resins, adipic acid-glycerol resins, and phthalic anhydride-pentaerythritol resins; allylic resins, in which such monomers as diallyl phthalate, diallyl isophthalate diallyl maleate, and diallyl chlorendate serve as nonvolatile cross-linking agents in polyester compounds; amino resins, such as aniline-formaldehyde resins, ethylene urea-formaldehyde resins, dicyandiamide-formaldehyde resins, melamine-formaldehyde resins, sulfonamide-formaldehyde resins, and urea-formaldehyde resins; epoxy resins, such as cross-linked epichlorohydrin-bisphenol A resins; phenolic resins, such as phenol-formaldehyde resins, including Novolacs and resols; and thermosetting polyesters, silicones, and urethanes.

In addition to the colorant, and ultraviolet radiation transorber, and optional vehicle, the colored composition may contain additional components, depending upon the application for which it is intended. For example, a composition which is to be utilized as a toner in an electrophotographic process that may be used to make the data processing forms of the present invention optionally can contain, for example, charge control agents, stabilizers against thermal oxidation, viscoelastic properties modifiers, cross-linking agents, plasticizers, and the like. Further, a composition which is to be utilized as a toner in an electrophotographic process optionally can contain charge control additives such as a quaternary ammonium salt; flow control additives such as hydrophobic silica, zinc stearate, calcium stearate, lithium stearate, polyvinylstearate, and polyethylene powders; and fillers such as calcium carbonate, clay and talc, among other additives used by those having ordinary skill in the art. For some applications, the charge control agent will be the major component of the toner. Charge control agents, of course, are well known to those having ordinary skill in the art and typically are polymer-coated metal particles. The identities and amounts of such additional components in the colored composition are well known to one of ordinary skill in the art. Further, the toner can also incorporate a molecular includant as described above.

It should be understood from the discussion above that the colored composition may be incorporated into printing fluids or other materials used in printing processes, image-creating processes, image-duplication processes or the like to generate indicia, marks, text, graphics or the like and/or define indicia-receiving locations "at about" or on at least one surface of a sheet of carrier material to prepare the data processing forms of the present invention.

Referring now to FIGS. 6 and 7, there is shown (not necessarily to scale) an illustration of two exemplary methods for optical scanning of the exemplary data processing forms addressed by the present invention. In each method, portions of a data processing form are sequentially scanned. This is usually accomplished by transporting the data processing form through a scanning station forming part of scanning equipment. Such equipment (not shown here) usually includes a tray or other means for holding forms to be scanned, transport means to pick up a single document at a time and move it through the scanning station and an output tray or other means for holding forms that have been scanned. As the form is transported through the scanning station, one or more photo-sensing apparatus is used to check for the presence or absence of indicia (e.g., marks) in specified areas (i.e., indicia-receiving locations). This photo-sensing apparatus generates electrical signals that are processed to discriminate between the presence or absence of a indicia. Data produced by the indicia discriminating circuitry may be further processed by comparison to a control or answer key, developing a total or totals for various indica and storing data associated with a particular data processing form and/or a group of data processing forms for further interpretation. Photo-sensing equipment of this general type is disclosed by sources such as, for example, U.S. Pat. Nos. 3,737,628 and 3,800,439.

FIG. 6 is an illustration of an exemplary photo-sensing apparatus based on the transmitted-read method. A data processing form 40 has a first or top surface 42 and a second or bottom surface 44. The top surface 42 may have a sequence of timing marks 50 forming a control mark column 52 (See FIG. 8). As best seen in FIG. 8, associated with the control marks 50 are a plurality of indicia-receiving locations 80 (e.g., response areas when the form 40 is used as a test answer sheet, a survey form, or the like). The form 40 may have control marks 50 and indicia-receiving locations 80 on only one surface or on both surfaces. Thus, FIG. 6 shows additional control marks 60 on the bottom surface 44. These are shown as aligned with and symmetrically located relative to the control marks 50 on the top surface, as may be required for transmitted-read type forms.

An exemplary photo-sensing apparatus that may be used in a transmitted-read method includes, as shown in FIG. 6, a light source 22 adjacent the top surface 42 and a photo-sensor 30 adjacent the bottom surface 44. The photo-sensor 30 receives light transmitted through the scannable form 40 which is made of a suitable material that allows at least the minimum level of light transmission to enable the transmitted-read equipment to function properly when no indicia (e.g., mark) is present to occlude the light. When an indicia is present, little or no light may reach the photo-sensor 30. The electrical output of the photo-sensor 30 is received by data processing means 32 and processed to discriminate between indicia (e.g., mark) and "non-indicia" (e.g., non-mark). (An exemplary scanner device using this scanning method is the Sentry 3000 scanner sold by National Computer Systems, Inc., of Eden Prairie, Minn. Other scanner devices using the transmitted-read method may be available from other sources).

The indicia-receiving locations 80 are positioned on the form 40 to have a particular orientation to the control marks 50. When the photo-sensor 30 detects a control mark 50, it triggers the photo-sensing apparatus to commence inspection for indicia which may or may not be present in indicia-receiving locations 80 associated with the control mark 50. Additionally, data processing forms that are processed by conventional transmitted-read methods should avoid having any light-absorbing or light-blocking material (e.g., marks, text, graphics, or the like) on the bottom surface 44 of the form that disrupt or interfere with light transmission through the form from indicia-receiving locations 80 on the top surface 42 (and vice versa, if the bottom surface 44 also has indicia-receiving locations 80 that are to be processed)

FIG. 7 shows a photo-sensing apparatus based on the reflective-read method. Equipment/systems of this type are disclosed by, for example, U.S. Pat. Nos. 3,676,690 and 4,300,123. For purposes of discussion, the data processing form 40 will be the same in both FIG. 6 and FIG. 7. An exemplary photo-sensing apparatus that may be used in the reflective-read method includes, as shown in FIG. 7, a pair of light sources 120, 122 placed adjacent the top surface 42 of the data-processing form 40 so as to direct reflected light to a photo-sensor 130 when indicia are absent from the indicia-receiving location 80. When an indicia is present, little or no light may be reflected to the photo-sensor 130. The electrical output of the photo-sensor 130 is received by data processing means 132 and processed in much the same manner as with transmitted-read photo-sensor 30 to discriminate between indicia (e.g., mark) and "non-indicia" (e.g., non-mark). To read both sides simultaneously, a further light source-photo-sensor combination can be placed adjacent the bottom surface 44 of the data processing form.

In view of the above, conventional photo-sensing apparatus, which may incorporate computer software and/or hardware, may be configured to inspect or "look" precisely at areas designated to contain indicia and not at other areas in order to discriminate between indicia (e.g., data marks), stray indicia (e.g., stray data marks), non-indicia (e.g., material not intended to be detected by photo-sensing apparatus), smudges, flaws in the document, or the like. Moreover, data processing forms can have applications in which only a few indicia-receiving locations are expected to contain indicia. In those situations, photo-sensing apparatus are designed or programmed to ignore indicia sensed in other areas. It is very desirable for the data processing form to be as free of clutter or markings which may interfere with the processing in order to simplify the design of the photo-sensing apparatus and to enhance the accuracy of processing the forms through the photo-sensing apparatus.

For example, FIGS. 8 and 9 are illustrations of a portion of an exemplary data processing form. This particular type of form contains indicia-receiving locations that are darkened and indicia-receiving locations that are filled in with alpha-numeric characters.

FIG. 8 illustrates a portion of a top surface 42 of an exemplary data processing form 40. The data processing form 40 has indicia-receiving locations 80 and other text 82 and graphics 84 defined by or formed from a mutable colored composition. The mutable colored composition is the colored composition described above and in the Examples. Some of the indicia-receiving locations 80 contain indicia 86. The top surface 42 of the data processing form 40 is depicted in FIG. 8 prior to irradiating the colored composition to irreversibly mutate the colorant.

The top surface 42 of the data processing form also contains control marks 50 and other markings 52 that are printed with conventional printing compositions (e.g., compositions containing colorants or pigments that do not mutate, that is, they remain detectable by the photo-sensing apparatus after being exposed to conditions that would cause the colorant of the mutable colored composition to irreversibly mutate).

FIG. 9 illustrates the exemplary data processing form shown in FIG. 8 after irradiating the colored composition to irreversibly mutate the colorant. As depicted in FIG. 9, the colorant used to define the indicia-receiving locations 80 and to form other text 82 and graphics 84 has been irreversibly mutated and rendered substantially undetectable (e.g., colorless or transparent), leaving only the control marks 50 and the indicia 86.

Accordingly, the data processing forms of the present invention provide an advantage in that any text, graphics, position markers (e.g., marks defining indicia-receiving locations), or other markings that should not be detected by the photo-sensing apparatus can be eliminated or otherwise rendered undetectable prior to processing the forms through the photo-sensing apparatus.

This objective may be accomplished with the data processing forms of the present invention. In one embodiment, the form is composed of: 1) a sheet of carrier material; and 2) a plurality of indicia-receiving locations on at least a first surface of the sheet. The indicia-receiving locations are defined by a colored composition including a mutable colorant and an ultraviolet radiation transorber. When the colored composition is irradiated with ultraviolet radiation at a dosage level sufficient to irreversibly mutate the colorant, the indicia-receiving locations are adapted to become substantially undetectable by photo-sensing apparatus. Desirably, the colored composition is irradiated with radiation in the ultraviolet region of the electromagnetic spectrum at a wavelength range between approximately 100 to 375 nanometers.

An embodiment of the method of practicing the method of the present invention (i.e., improving the readability of a data processing form used in photo-sensing apparatus that detect the presence of indicia in indica-receiving locations on the form) is based on utilizing data processing forms that have indicia-receiving locations defined by the colored compositions described above and in the Examples.

The steps of the method of the present invention are straightforward and can be described as follows:

providing a data processing form that includes a sheet of carrier material and indicia located at a plurality of indicia-receiving locations on at least a first surface of the sheet, the indicia-receiving locations being defined by a mutable colored composition comprising a mutable colorant and an ultraviolet radiation transorber, irradiating the colored composition with ultraviolet radiation at a dosage level sufficient to irreversibly mutate the colorant so that the indicia-receiving locations are substantially undetectable by photo-sensing apparatus, leaving the indicia to be detected.

Desirably, the colored composition is irradiated with radiation in the ultraviolet region of the electromagnetic spectrum at a wavelength of from about 100 to about 375 nanometers. As another example, the ultraviolet radiation may be incoherent, pulsed ultraviolet radiation from a dielectric barrier discharge excimer lamp.

The data processing form may be irradiated individually as part of a continuous irradiation step or the forms may be irradiated in batches (after entry of the appropriate indicia at the indicia-receiving locations) and then stored for any period of time prior to being introduced into the photo-sensing apparatus. Alternatively, the data processing forms may be irradiated as part of a continuous process that includes a step of introducing the forms into a photo-sensing apparatus.

Demonstrations of mutable colored compositions coated onto a carrier material (which may be in the form of text, graphics and indicia-receiving locations) and their subsequent irreversible mutation by exposure to ultraviolet radiation are set forth in Examples 1, 2, 3 and 4 below. Particular description of exemplary electromagnetic radiation generating equipment that produces an environment capable of irreversibly mutating the colored composition described herein is set forth in Examples 10, 11 and 12 as well as the associated Figures.

The method of the present invention is adaptable to work with transmitted-read data processing forms and/or reflective-read data processing forms. It is contemplated that intermediate steps may be incorporated into the method of the present invention. It is further contemplated that other formats of data processing forms may be used if it is desired that text, graphics, position markers (e.g., marks defining indicia-receiving locations), or other markings that should not be detected by the photo-sensing apparatus are to be eliminated or otherwise render undetectable prior to processing the forms through the photo-sensing apparatus.

Many data processing forms also have the limitations related to the indicia intended to be detected by photo-sensing apparatus. If the indicia is pre-printed prior to scanning, it is often very difficult or even impossible to modify or erase the indicia prior to processing. In many situations, it may be desirable to quickly and efficiently erase or modify indicia that are to be detected by photo-sensing apparatus. For example, data processing forms that contain indicia (e.g., dots, shapes, alpha-numeric characters, lines, bars or the like) in so many formats (e.g., coupons, packaging labels, parts labels or tags, inventory labels or tags, assembly-line work-in-progress labels or tags, baggage handling labels or tags, medical labels or tags, checks, identification cards, admission cards, admission tickets, credit cards, monetary instruments, transportation tickets, bar code stickers, bills, or the like) are used in such large numbers that the cost of reprinting or replacing the indicia on each item simply to change or alter the indicia could become significant. For example, FIGS. 10 and 11 are illustrations of a portion of an exemplary data processing form. This particular type of form contains indicia in the format of vertical bars intended to be detected or read by a photo-sensing apparatus utilizing the reflective-read method.

FIG. 10 illustrates an exemplary data processing form 200 having only a portion of the indicia 220 formed from the mutable colored composition described above and in the Examples prior to irradiating the colored composition to irreversibly mutate the colorant. The indicia 220 on data-processing form 200 shown in FIG. 10 is in the ubiquitous "bar code" format. Indicia in such a format typically is processed by laser "reflective-read" photo-sensing apparatus.

FIG. 11 illustrates the same exemplary data processing form 200 after irradiating the colored composition to irreversibly mutate the colorant. As is shown in the illustration, the colorant used to form several of the indicia has been irreversibly mutated and rendered substantially undetectable (e.g., colorless or transparent), effecting the desired modification of the indicia.

Accordingly, the data processing forms of the present invention provide an advantage in that it is possible to modify or erase indicia formed from the mutable colored composition in a data-processing form without reprinting or replacing the indicia on each item.

This objective can be accomplished by the data processing forms of the present invention. An embodiment of the present invention encompasses a data processing form that includes a plurality of mutable indicia. At least a portion of the indicia are formed from a mutable colored composition as described above and in the Examples. The colored composition includes a mutable colorant and an ultraviolet radiation transorber. When the colored composition is irradiated with ultraviolet radiation at a dosage level sufficient to irreversibly mutate the colorant, the indicia that are formed from the colored composition are adapted to become substantially undetectable by photo-sensing apparatus. Desirably, the colored composition is irradiated with radiation in the ultraviolet region of the ultraviolet spectrum. For example, the colored composition may be irradiated with ultraviolet radiation at a wavelength of from about 100 to about 375 nanometers. As another example, the ultraviolet radiation may be incoherent, pulsed ultraviolet radiation from a dielectric barrier discharge excimer lamp.

The method of practicing an embodiment of the method of the present invention (i.e., modifying indicia on a data processing form used in photo-sensing apparatus that detect the presence of indicia at indica-receiving locations on the form) is based on utilizing data processing forms that have at least some indicia formed from the colored compositions described above and in the Examples.

The steps of the method of the present invention are straightforward and can be described as follows:

providing a data processing form that includes a sheet of carrier material and a plurality of indicia at indicia-receiving locations on at least a first surface of the sheet, at least a portion of the indicia being mutable indicia formed from a colored composition including a mutable colorant and an ultraviolet radiation transorber;

irradiating the colored composition with ultraviolet radiation at a dosage level sufficient to irreversibly mutate the colorant so that at least a portion of the mutable indicia are substantially undetectable by photo-sensing apparatus.

The data processing form may be irradiated individually as part of a continuous irradiation step or the forms may be irradiated in batches (after entry of the appropriate indicia in the indicia-receiving locations) and then stored for any period of time prior to being introduced into the photo-sensing apparatus. Alternatively, the data processing forms may be irradiated as part of a continuous process that includes a step of introducing the forms into a photo-sensing apparatus.

Demonstrations of mutable colored compositions coated onto a carrier material (which may be in the form of mutable indicia) and their subsequent irreversible mutation by exposure to ultraviolet radiation are set forth in Examples 1, 2, 3 and 4 below. Particular description of exemplary electromagnetic radiation generating equipment that produces an environment capable of irreversibly mutating the colored composition described herein is set forth in Examples 10, 11 and 12 as well as the associated Figures.

The method of the present invention is adaptable to work with transmitted-read data processing forms and/or reflective-read data processing forms. It is contemplated that intermediate steps may be incorporated into the method of the present invention. It is further contemplated that other formats of data processing forms may be used if it is desired to modify or erase indicia from the data processing forms prior to processing the forms through the photo-sensing apparatus.

Aspects of the present invention are further described by the examples that follow. Such examples, however, are not to be construed as limiting in any way either the spirit or scope of the present invention. In the examples, all parts are parts by weight unless stated otherwise.

EXAMPLE 1

This example describes the preparation of films consisting of colorant, ultraviolet radiation transorber, and thermoplastic polymer. The colorant and ultraviolet radiation transorber were ground separately in a mortar. The desired amounts of the ground components were weighed and placed in an aluminum pan, along with a weighed amount of a thermoplastic polymer. The pan was placed on a hot plate set at 150° C. and the mixture in the pan was stirred until molten. A few drops of the molten mixture were poured onto a steel plate and spread into a thin film by means of a glass microscope slide. Each steel plate was 3×5 inches (7.6 cm×12.7 cm) and was obtained from Q-Panel Company, Cleveland, Ohio. The film on the steel plate was estimated to have a thickness of the order of 10–20 micrometers.

In every instance, the colorant was Malachite Green oxalate (Aldrich Chemical Company, Inc., Milwaukee, Wis.), referred to hereinafter as Colorant A for convenience. The ultraviolet radiation transorber ("UVRT") consisted of one or more of IRGACURE® 500 ("UVRT A"), IRGACURE® 651 ("UVRT B"), and IRGACURE® 907 ("UVRT C"), each of which was described earlier and is available from Ciba-Geigy Corporation, Hawthorne, N.Y. The polymer was one of the following: an epichlorohydrin-bisphenol A epoxy resin ("Polymer A"), EPON® 1004F (Shell Oil Company, Houston, Tex.); a poly(ethylene glycol) having a weight-average molecular weight of about 8,000 ("Polymer B"), CARBOWAX® 8000 (Aldrich Chemical Company); and a poly(ethylene glycol) having a weight-average molecular weight of about 4,600 ("Polymer C"), CARBOWAX® 4600 (Aldrich Chemical Company). A control film was prepared which consisted only of colorant and polymer. The compositions of the films are summarized in Table 1.

TABLE 1

Compositions of Films Containing Colorant and Ultraviolet Radiation Transorber "UVRT"

| Film | Colorant Type | Colorant Parts | UVRT Type | UVRT Parts | Polymer Type | Polymer Parts |
|---|---|---|---|---|---|---|
| A | A | 1 | A | 6 | A | 90 |
|   |   |   | C | 4 |   |   |
| B | A | 1 | A | 12 | A | 90 |
|   |   |   | C |   |   |   |
| C | A | 1 | A | 18 | A | 90 |
|   |   |   | C | 12 |   |   |
| D | A | 1 | A | 6 | A | 90 |
|   |   |   | B | 4 |   |   |
| E | A | 1 | B | 30 | A | 70 |
| F | A | 1 | — | — | A | 100 |
| G | A | 1 | A | 6 | B | 90 |
|   |   |   | C | 4 |   |   |
| H | A | 1 | B | 10 | C | 90 |

While still on the steel plate, each film was exposed to ultraviolet radiation. In each case, the steel plate having the film sample on its surface was placed on a moving conveyor belt having a variable speed control. Three different ultraviolet radiation sources, or lamps, were used. Lamp A was a 222-nanometer excimer lamp and Lamp B was a 308-nanometer excimer lamp, as already described. Lamp C was a fusion lamp system having a "D" bulb (Fusion Systems Corporation, Rockville, Md.). The excimer lamps were organized in banks of four cylindrical lamps having a length of about 30 cm, with the lamps being oriented normal to the direction of motion of the belt. The lamps were cooled by circulating water through a centrally located or inner tube of the lamp and, as a consequence, they operated at a relatively low temperature, i.e., about 50° C. The power density at the lamp's outer surface typically is in the range of from about 4 to about 20 joules per square meter ($J/m^2$).

However, such range in reality merely reflects the capabilities of current excimer lamp power supplies; in the future, higher power densities may be practical. With Lamps A and B, the distance from the lamp to the film sample was 4.5 cm and the belt was set to move at 20 ft/min (0.1 m/sec). With Lamp C, the belt speed was 14 ft/min (0.07 m/sec) and the lamp-to-sample distance was 10 cm. The results of exposing the film samples to ultraviolet radiation are summarized in Table 2. Except for Film F, the table records the number of passes under a lamp which were required in order to render the film colorless. For Film F, the table records the number of passes tried, with the film in each case remaining colored (no change).

TABLE 2

Results of Exposing Films Containing Colorant and Ultraviolet Radiation Transorber (UVRT) to Ultraviolet Radiation

| Film | Excimer Lamp A | Excimer Lamp B | Fusion Lamp |
|---|---|---|---|
| A | 3 | 3 | 15 |
| B | 2 | 3 | 10 |
| C | 1 | 3 | 10 |
| D | 1 | 1 | 10 |
| E | 1 | 1 | 1 |
| F | 5 | 5 | 10 |
| G | 3 | — | 10 |
| H | 3 | — | 10 |

EXAMPLE 2

This example describes the preparation of solid colored compositions adapted to be utilized as toners in an electrophotographic process. In every instance, the toner included Colorant A as described in Example 1; a polymer, DER 667, an epichlorohydrin-bisphenol A epoxy resin (Polymer D), EPON® 1004F (Dow Chemical Company, Midland, Mich.); and a charge control agent, Carrier A, which consisted of a very finely divided polymer-coated metal. The ultraviolet radiation transorber (UVRT) consisted of one or more of UVRT B from Example 1, IRGACURE® 369 (UVRT D), and IRGACURE® 184 (UVRT E); the latter two transorbers were described earlier and are available from Ciba-Geigy Corporation, Hawthorne, N.Y. In one case, a second polymer also was present, styrene acrylate 1221, a styrene-acrylic acid copolymer (Hercules Incorporated, Wilmington, Del.).

To prepare the toner, colorant, ultraviolet radiation transorber, and polymer were melt-blended in a Model 3VV 800E, 3 inch×7 inch (7.6 cm×17.8 cm) two-roll research mill (Farrel Corporation, Ansonia, Conn.). The resulting melt-blend was powdered in a Mikropul hammermill with a 0.010-inch herringbone screen (R. D. Kleinfeldt, Cincinnati, Ohio) and then sieved for proper particle sizes in a Sturtvant, air two-inch micronizer (R. D. Kleinfeldt) to give what is referred to herein as a pretoner. Charge control agent then was added to the pretoner and the resulting mixture blended thoroughly. Table 3 summarizes the compositions of the pretoners and Table 4 summarizes the compositions of the toners.

TABLE 3

Summary of Pretoner Compositions

| Pretoner | Colorant A (g) | UVRT Type | g | Polymer Type | g |
|---|---|---|---|---|---|
| A | 1 | D | 20 | D | 80 |
| B | 1 | B | 20 | D | 80 |
| C | 1 | B | 10 | D | 80 |
|   |   | D | 10 |   |   |
| D | 1 | B | 6.9 | D | 40 |
|   |   | D | 6.6 | E | 40 |
|   |   | E | 6.6 |   |   |

TABLE 4

Summary of Toner Compositions

| Toner | Pretoner Type | g | Charge Control Agent (g) |
|---|---|---|---|
| A | A | 8.4 | 210 |
| B | B | 8.4 | 210 |
| C | C | 8.4 | 210 |
| D | D | 8.4 | 210 |

Each toner was placed separately in a Sharp Model ZT-50TD1 toner cartridge and installed in either a Sharp Model Z-76 or a Sharp Model Z-77 xerographic copier (Sharp Electronics Corporation, Mahwah, N.J.). Images were made in the usual manner on bond paper (Neenah Bond). The image-bearing sheets then were exposed to ultraviolet radiation from Lamp B as described in Example 1. In each case, the image was rendered colorless with one pass.

EXAMPLE 3

This example describes the preparation of a β-cyclodextrin molecular includant having (1) an ultraviolet radiation transorber covalently bonded to the cyclodextrin outside of the cavity of the cyclodextrin and (2) a colorant associated with the cyclodextrin by means of hydrogen bonds and/or van der Waals forces.

A. Friedel-Crafts Acylation of Transorber

A 250-ml, three-necked, round-bottomed reaction flask was fitted with a condenser and a pressure-equalizing addition funnel equipped with a nitrogen inlet tube. A magnetic stirring bar was placed in the flask. While being flushed with nitrogen, the flask was charged with 10 g (0.05 mole) of 1-hydroxycyclohexyl phenyl ketone (IRGACURE® 184, Ciba-Geigy Corporation, Hawthorne, N.Y.), 100 ml of anhydrous tetrahydofuran (Aldrich Chemical Company, Inc., Milwaukee, Wis.), and 5 g (0.05 mole) of succinic anhydride (Aldrich). To the continuously stirred contents of the flask then was added 6.7 g of anhydrous aluminum chloride (Aldrich). The resulting reaction mixture was maintained at about 0° C. in an ice bath for about one hour, after which the mixture was allowed to warm to ambient temperature for two hours. The reaction mixture then was poured into a mixture of 500 ml of ice water and 100 ml of diethyl ether. The ether layer was removed after the addition of a small amount of sodium chloride to the aqueous phase to aid phase separation. The ether layer was dried over anhydrous magnesium sulfate. The ether was removed under reduced pressure, leaving 12.7 g (87 percent) of a white crystalline powder. The material was shown to be 1-hydroxycyclohexyl 4-(2-carboxyethyl)carbonylphenyl ketone by nuclear magnetic resonance analysis.

B. Preparation of Acylated Transorber Acid Chloride

A 250-ml round-bottomed flask fitted with a condenser was charged with 12.0 g of 1-hydroxycyclohexyl 4-(2-carboxyethyl)carbonylphenyl ketone (0.04 mole), 5.95 g (0.05 mole) of thionyl chloride (Aldrich), and 50 ml of diethyl ether. The resulting reaction mixture was stirred at 30° C. for 30 minutes, after which time the solvent was removed under reduced pressure. The residue, a white solid, was maintained at 0.01 Torr for 30 minutes to remove residual solvent and excess thionyl chloride, leaving 12.1 g (94 percent) of 1-hydroxycyclohexyl 4-(2-chloroformylethyl)carbonylphenyl ketone.

C. Covalent Bonding of Acylated Transorber to Cyclodextrin

A 250-ml, three-necked, round-bottomed reaction flask containing a magnetic stirring bar and fitted with a thermometer, condenser, and pressure-equalizing addition funnel equipped with a nitrogen inlet tube was charged with 10 g (8.8 mmole) of β-cyclodextrin (American Maize-Products Company, Hammond, Ind.), 31.6 g (98 mmoles) of 1-hydroxycyclohexyl 4-(2-chloroformylethyl) carbonylphenyl ketone, and 100 ml of N,N-dimethylformamide while being continuously flushed with nitrogen. The reaction mixture was heated to 50° C. and 0.5 ml of triethylamine added. The reaction mixture was maintained at 50° C. for an hour and allowed to cool to ambient temperature. In this preparation, no attempt was made to isolate the product, a β-cyclodextrin to which an ultraviolet radiation transorber had been covalently coupled (referred to hereinafter for convenience as β-cyclodextrin-transorber).

The foregoing procedure was repeated to isolate the product of the reaction. At the conclusion of the procedure as described, the reaction mixture was concentrated in a rotary evaporator to roughly 10 percent of the original volume. The residue was poured into ice water to which sodium chloride then was added to force the product out of solution. The resulting precipitate was isolated by filtration and washed with diethyl ether. The solid was dried under reduced pressure to give 24.8 g of a white powder. In a third preparation, the residue remaining in the rotary evaporator was placed on top of an approximately 7.5-cm column containing about 15 g of silica gel. The residue was eluted with N,N-dimethylformamide, with the eluant being monitored by means of WHATMAN® Flexible-Backed TLC Plates (Catalog No. 05–713–161, Fisher Scientific, Pittsburgh, Pa.). The eluted product was isolated by evaporating the solvent. The structure of the product was verified by nuclear magnetic resonance analysis.

D. Association of Colorant with Cyclodextrin-Transorber—Preparation of Colored Composition To a solution of 10 g (estimated to be about 3.6 mmole) of beta-cyclodextrin-transorber in 150 ml of N,N-dimethylformamide in a 250-ml round-bottomed flask was added at ambient temperature 1.2 g (3.6 mmole) of Malachite Green oxalate (Aldrich Chemical Company, Inc., Milwaukee, Wis.), referred to hereinafter as Colorant A for convenience. The reaction mixture was stirred with a magnetic stirring bar for one hour at ambient temperature. Most of the solvent then was removed in a rotary evaporator and the residue was eluted from a silica gel column as already described. The beta-cyclodextrin-transorber Colorant A inclusion complex moved down the column first, cleanly separating from both free Colorant A and beta-cyclodextrin-transorber. The eluant containing the complex was collected and the solvent removed in a rotary evaporator. The residue was subjected to a reduced pressure of 0.01 Torr to remove residual solvent to yield a blue-green powder.

E. Mutation of Colored Composition

The beta-cyclodextrin-transorber Colorant A inclusion complex was exposed to ultraviolet radiation from two different lamps, Lamps A and B. Lamp A was a 222-nanometer excimer lamp assembly organized in banks of four cylindrical lamps having a length of about 30 cm. The lamps were cooled by circulating water through a centrally located or inner tube of the lamp and, as a consequence, they operated at a relatively low temperature, i.e., about 50° C. The power density at the lamp's outer surface typically is in the range of from about 4 to about 20 joules per square meter ($J/m^2$). However, such range in reality merely reflects the capabilities of current excimer lamp power supplies; in the future, higher power densities may be practical. The distance from the lamp to the sample being irradiated was 4.5 cm. Lamp B was a 500-watt Hanovia medium pressure mercury lamp (Hanovia Lamp Co., Newark, N.J.). The distance from Lamp B to the sample being irradiated was about 15 cm.

A few drops of an N,N-dimethylformamide solution of the beta-cyclodextrin-transorber Colorant A inclusion complex were placed on a TLC plate and in a small polyethylene weighing pan. Both samples were exposed to Lamp A and were decolorized (mutated to a colorless state) in 15–20 seconds. Similar results were obtained with Lamp B in 30 seconds.

A first control sample consisting of a solution of Colorant A and beta-cyclodextrin in N,N-dimethylformamide was not decolorized by Lamp A. A second control sample consisting of Colorant A and 1-hydroxycyclohexyl phenyl ketone in N,N-dimethylformamide was decolorized by Lamp A within 60 seconds. On standing, however, the color began to reappear within an hour.

To evaluate the effect of solvent on decolorization, 50 mg of the beta-cyclodextrin-transorber Colorant A inclusion complex was dissolved in 1 ml of solvent. The resulting solution or mixture was placed on a glass microscope slide and exposed to Lamp A for 1 minute. The rate of decolorization, i.e., the time to render the sample colorless, was directly proportional to the solubility of the complex in the solvent, as summarized below.

| Solvent | Solubility | Decolorization Time |
| --- | --- | --- |
| N,N-Dimethylformamide | Poor | 1 minute |
| Dimethylsulfoxide | Soluble | <10 seconds |
| Acetone | Soluble | 10 seconds |
| Hexane | Insoluble | — |
| Ethyl Acetate | Poor | 1 minute |

Finally, 10 mg of the beta-cyclodextrin-transorber Colorant A inclusion complex were placed on a glass microscope slide and crushed with a pestle. The resulting powder was exposed to Lamp A for 10 seconds. The powder turned colorless. Similar results were obtained with lamp B, but at a slower rate.

EXAMPLE 4

Because of the possibility in the preparation of colored composition described in Example 3 for the acylated transorber acid chloride to at least partially occupy the cavity of the cyclodextrin, to the partial or complete exclusion of colorant, a modified preparative procedure was carried out. Thus, this example describes the preparation of a beta-cyclodextrin molecular includant having (1) a colorant at least partially included within the cavity of the cyclodextrin and associated therewith by means of hydrogen bonds and/or van der Waals forces and (2) an ultraviolet radiation transorber covalently bonded to the cyclodextrin outside of the cavity of the cyclodextrin.

A. Association of Colorant with a Cyclodextrin

To a solution of 10.0 g (8.8 mmole) of beta-cyclodextrin in 150 ml of N,N-dimethylformamide was added 3.24 g (9.6 mmoles) of Colorant A. The resulting solution was stirred at ambient temperature for one hour. The reaction solution was concentrated under reduced pressure in a rotary evaporator to a volume about one-tenth of the original volume. The residue was passed over a silica gel column as described in Part C of Example 1. The solvent in the eluant was removed under reduced pressure in a rotary evaporator to give 12.4 g of a blue-green powder, beta-cyclodextrin Colorant A inclusion complex.

B. Covalent Bonding of Acylated Transorber to Cyclodextrin Colorant Inclusion Complex—Preparation of Colored Composition A 250 ml, three-necked, round-bottomed reaction flask containing a magnetic stirring bar and fitted with a thermometer, condenser, and pressure-equalizing addition funnel equipped with a nitrogen inlet tube was charged with 10 g (9.6 mmole) of beta-cyclodextrin Colorant A inclusion complex, 31.6 g (98 mmoles) of 1-hydroxycyclohexyl 4-(2-chloroformylethyl)carbonylphenyl ketone prepared as described in Part 3 of Example 1, and 150 ml of N,N-dimethylformamide while being continuously flushed with nitrogen. The reaction mixture was heated to 50° C. and 0.5 ml of triethylamine added. The reaction mixture was maintained at 50° C. for an hour and allowed to cool to ambient temperature. The reaction mixture then was worked up as described in Part A, above, to give 14.2 g of beta-cyclodextrin-transorber Colorant A inclusion complex, a blue-green powder.

C. Mutation of Colored Composition

The procedures described in Part E of Example 1 were repeated with the beta-cyclodextrin-transorber Colorant A inclusion complex prepared in part B, above, with essentially the same results.

EXAMPLE 5

This Example describes a method of preparing an ultraviolet radiation transorber designated phthaloylglycine-2959.

The following was admixed in a 250 ml 3-necked round bottomed flask fitted with a Dean & Stark adapter with condenser and two glass stoppers: 20.59 g (0.1 mole) of the wavelength selective sensitizer, phthaloylglycine (Aldrich) 24.6 g (0.1 mole) of the photoreactor, IRGACUR® 2959 (Ciba-Geigy, Hawthorne, N.Y.); 100 ml of benzene (Aldrich); and 0.4 g p-toluene sulfonic acid (Aldrich). The mixture was heated at reflux for 3 hours after which time 1.8 ml of water was collected. The solvent was removed under reduced pressure to give 43. g of white powder. The powder was recrystallized from 30% ethyl acetate in hexane (Fisher) to yield 40.2 g (93%) of a white crystalline powder having a melting point of 153–4° C. The resulting product, designated phthaloyl glycine-2959, had the following physical parameters:

IR [Nujol Mull]] $v_{max}$ 3440, 1760, 1740, 1680, 1600 $cm^{-1}$ $^1$HNMR [$CDCL_3$] δppm 1.64[s], 4.25[m], 4.49[m], 6.92 [m], 7.25[m], 7.86[m], 7.98[m], 8.06[m] ppm

EXAMPLE 6

This Example describes a method of dehydrating the phthaloylglycine-2959 produced in Example 5.

The following was admixed in a 250 ml round bottomed flask fitted with a Dean & Stark adaptor with condenser: 21.6 g (0.05 mole) phthaltoylglycine-2959; 100 ml of anhydrous benzene (Aldrich); and 0.1 g p-toulene sulfonic acid (Aldrich). The mixture was refluxed for 3 hours. After 0.7 ml of water had been collected in the trap, the solution was then removed under vacuum to yield 20.1 g (97%) of a white solid. The solid was used without further purification.

The resulting reaction product had the following physical parameters:

IR (NUJOL) $v_{max}$ 1617cm$^{-1}$ (C=C—C=O)

EXAMPLE 7

This Example describes a method of producing a beta-cyclodextrin having dehydrated phthaloylglycine-2959 groups from Example 6 covalently bonded thereto.

The following was admixed in a 100 ml round bottomed Flask: 5.0 g (4.4 mmole) beta-cyclodextrin (American Maize Product Company, Hammond, Ind.) (designated beta-CD in the following reaction); 8.3 g (20 mmole) dehydrated phthaloylglycine-2959; 50 ml of anhydrous DMF; 20 ml of benzene; and 0.01 g p-tolulenesulfonyl chloride (Aldrich). The mixture was chilled in a salt/ice bath and stirred for 24 hours. The reaction mixture was poured into 150 ml of weak sodium bicarbonate solution and extracted three times with 50 ml ethyl ether. The aqueous layer was then filtered to yield a white solid comprising the beta-cyclodextrin with phthaloylglycine-2959 group attached. A yield of 9.4 g was obtained. Reverse phase TLC plate using a 50:50 DMF:acetonitrile mixture showed a new product peak compared to the starting materials.

Of course, the beta-cyclodextrin molecule has several primary alcohols and secondary alcohols with which the phthaloylglycine-2959 can react.

EXAMPLE 8

This example describes a method of associating a colorant and an ultraviolet radiation transorber with a molecular includant. More particularly, this Example describes a method of associating the colorant crystal violet with the molecular includant beta-cyclodextrin covalently bonded to the ultraviolet radiation transorber phthaloylglycine-2959 of Example 7.

The following was placed in a 100 ml beaker: 4.0 g beta-cyclodextrin having a dehydrated phthaloylglycine-2959 group; and 50 ml of water. The water was heated to 70° C. at which point the solution became clear. Next, 0.9 g (2.4 mmole) crystal violet (Aldrich Chemical Company, Milwaukee, Wis.) was added to the solution, and the solution was stirred for 20 minutes. Next, the solution was then filtered. The filtrand was washed with the filtrate and then dried in a vacuum oven at 84° C. A violet-blue powder was obtained having 4. g (92%) yield. The resulting reaction product had the following physical parameters:

U.V. Spectrum DMF $\Lambda_{max}$ 610 nm (cf cv $\Lambda_{max}$ 604 nm)

EXAMPLE 9

This Example describes a method of producing the ultraviolet radiation transorber 4(4-hydroxyphenyl) butan-2-one-2959 (chloro substituted).

The following was admixed in a 250 ml round bottomed flask fitted with a condenser and magnetic stir bar: 17.6 g (0.1 mole) of the wavelength selective sensitizer, 4(4-hydroxyphenyl) butan-2-one (Aldrich Chemical Company, Milwaukee, Wis.); 26.4 g (0.1 mole) of the photoreactor, chloro substituted IRGACURE® 2959 (Ciba-Geigy Corporation, Hawthorne, N.Y.); 1.0 ml of pyridine (Aldrich Chemical Company, Milwaukee, Wis.); and 100 ml of anhydrous tetrahydrofuran (Aldrich Chemical Company, Milwaukee, Wis.). The mixture was refluxed for 3 hours and the solvent partially removed under reduced pressure (60% taken off). The reaction mixture was then poured into ice water and extracted with two 50 ml aliquots of diethyl ether. After drying over anhydrous magnesium sulfate and removal of solvent, 39. g of white solvent remained. Recrystallization of the powder from 30% ethyl acetate in hexane gave 36.7 g (91%) of a white crystalline powder, having a melting point of 142–143° C.

The resulting reaction product had the following physical parameters:

IR [Nujol Mull] $\nu^{max}$ 3460, 1760, 1700, 1620, 1600 cm$^{-1}$ $^1$H [CDCL$_3$] δppm 1.62[s], 4.2[m], 4.5[m], 6.9[m] ppm The ultraviolet radiation transorber produced in this Example, 4(4-hydroxyphenyl) butan-2-one-2959 (chloro substituted), may be associated with beta-cyclodextrin and a colorant such as crystal violet, using the methods described above in Examples 6 through 8 wherein 4 (4-hydroxyphenyl) butan-2-one-2959 (chloro substituted) would be substituted for the dehydrated phthaloylglycine-2959 in the methods in Examples 6 through 8.

EXAMPLE 10

This Example demonstrates that the 222 nanometer excimer lamps illustrated in FIG. 3 produce uniform intensity readings on a surface of a substrate 5.5 centimeters from the lamps, at the numbered locations, in an amount sufficient to mutate the colorant in the compositions of the present invention which are present on the surface of the substrate. The lamp 10 comprises a lamp housing 15 with four excimer lamp bulbs 20 positioned in parallel, the excimer lamp bulbs 20 are approximately 30 cm in length. The lamps are cooled by circulating water through a centrally located or inner tube (not shown) and, as a consequence, the lamps are operated at a relatively low temperature, i.e., about 50° C. The power density at the lamp's outer surface typically is in the range of from about 4 to about 20 joules per square meter (J/m$^2$).

Table 5 summarizes the intensity readings which were obtained by a meter located on the surface of the substrate. The readings numbered 1, 4, 7, and 10 were located approximately 7.0 centimeters from the left end of the column as shown in FIG. 3. The readings numbered 3, 6, 9, and 12 were located approximately 5.5 centimeters from the right end of the column as shown in FIG. 3. The readings numbered 2, 5, 8, and 11 were centrally located approximately 17.5 centimeters from each end of the column as shown in FIG. 3.

TABLE 5

| Background ($\mu$W) | Reading (mW/cm$^2$) |
|---|---|
| 24.57 | 9.63 |
| 19.56 | 9.35 |
| 22.67 | 9.39 |
| 19.62 | 9.33 |
| 17.90 | 9.30 |
| 19.60 | 9.30 |
| 21.41 | 9.32 |

TABLE 5-continued

| Background (μW) | Reading (mW/cm²) |
|---|---|
| 17.91 | 9.30 |
| 23.49 | 9.30 |
| 19.15 | 9.36 |
| 17.12 | 9.35 |
| 21.44 | 9.37 |

EXAMPLE 11

This Example demonstrates that the 222 nanometer excimer lamps illustrated in FIG. 4 produce uniform intensity readings on a surface of a substrate 5.5 centimeters from the lamps, at the numbered locations, in an amount sufficient to mutate the colorant in the compositions of the present invention which are present on the surface of the substrate. The excimer lamp 10 comprises a lamp housing 15 with four excimer lamp bulbs 20 positioned in parallel, the excimer lamp bulbs 20 are approximately 30 cm in length. The lamps are cooled by circulating water through a centrally located or inner tube (not shown) and, as a consequence, the lamps are operated at a relatively low temperature, i.e., about 50° C. The power density at the lamp's outer surface typically is in the range of from about 4 to about 20 joules per square meter (J/m²).

Table 6 summarizes the intensity readings which were obtained by a meter located on the surface of the substrate. The readings numbered 1, 4, and 7 were located approximately 7.0 centimeters from the left end of the columns as shown in FIG. 4. The readings numbered 3, 6, and 9 were located approximately 5.5 centimeters from the right end of the columns 40 as shown in FIG. 4. The readings numbered 2, 5, 8 were centrally located approximately 17.5 centimeters from each end of the columns as shown in FIG. 4.

TABLE 6

| Background (μW) | Reading (mW/cm²) |
|---|---|
| 23.46 | 9.32 |
| 16.12 | 9.31 |
| 17.39 | 9.32 |
| 20.19 | 9.31 |
| 16.45 | 9.29 |
| 20.42 | 9.31 |
| 18.33 | 9.32 |
| 15.50 | 9.30 |
| 20.90 | 9.34 |

EXAMPLE 12

This Example demonstrates the intensity produced by the 222 nanometer excimer lamps illustrated in FIG. 5, on a surface of a substrate, as a function of the distance of the surface from the lamps, the intensity being sufficient to mutate the colorant in the compositions of the present invention which are present on the surface of the substrate. The excimer lamp 10 comprises a lamp housing 15 with four excimer lamp bulbs 20 positioned in parallel, the excimer lamp bulbs 20 are approximately 30 cm in length. The lamps are cooled by circulating water through a centrally located or inner tube (not shown) and, as a consequence, the lamps are operated at a relatively low temperature, i.e., about 50° C. The power density at the lamp's outer surface typically is in the range of from about 4 to about 20 joules per square meter (J/m²)

Table 7 summarizes the intensity readings which were obtained by a meter located on the surface of the substrate at position 1 as shown in FIG. 5. Position 1 was centrally located approximately 17 centimeters from each end of the column as shown in FIG. 5.

TABLE 7

| Distance (cm) | Background (μW) | Reading (mW/cm²) |
|---|---|---|
| 5.5 | 18.85 | 9.30 |
| 6.0 | 15.78 | 9.32 |
| 10 | 18.60 | 9.32 |
| 15 | 20.90 | 9.38 |
| 20 | 21.67 | 9.48 |
| 25 | 19.86 | 9.69 |
| 30 | 22.50 | 11.14 |
| 35 | 26.28 | 9.10 |
| 40 | 24.71 | 7.58 |
| 50 | 26.95 | 5.20 |

Having thus described the invention, numerous changes and modifications hereof will be readily apparent to those having ordinary skill in the art without departing from the spirit or scope of the invention.

What is claimed is:

1. A data processing form for use with photo-sensing apparatus that detect the presence of indicia at indicia-receiving locations on the form, the form comprising:
   a sheet of carrier material; and
   a mutable colored composition on at least a first surface of the sheet, the mutable colored composition comprising a mutable colorant a molecular includant and an ultraviolet radiation transorber, the ultraviolet radiation transorber having an absorption maximum corresponding to a substantially single wavelength of ultraviolet radiation from a dielectric barrier discharge excimer lamp;
   wherein the mutable colored composition becomes substantially undetectable by the photo-sensing apparatus upon irradiating with the excimer lamp.

2. The data processing form of claim 1, wherein the mutable colored composition is present on the first surface of the sheet in the form of indicia-receiving locations.

3. The data processing form of claim 1, wherein the mutable colored composition is present on the first surface of the sheet in the form of indicia.

4. The data processing form of claim 1, wherein the molecular includant is selected from the group consisting of clathrates, zeolites, and cyclodextrins.

5. The data processing form of claim 1, wherein the mutable colored composition is in the form of text or graphics.

6. The data processing form of claim 1, wherein the form is a transmitted-read form or a reflective-read form.

7. The data processing form of claim 1, wherein the carrier material is substantially opaque, transparent or translucent.

8. The data processing form of claim 1, wherein the substantially single wavelength is from about 125 nanometers to about 360 nanometers.

9. The data processing form of claim 8, wherein the substantially single wavelength is about 222 nanometers.

10. The data processing form of claim 1, wherein the molecular includant is covalently bonded to the ultraviolet radiation transorber.

11. A method for improving the readability of a data processing form used in a photo-sensing apparatus that detects the presence of indicia at indicia-receiving locations on the form, the method comprising:

providing a data processing form comprising a sheet of carrier material and a mutable colored composition on at least a first surface of the sheet, the mutable colored composition comprising a mutable colorant and an ultraviolet radiation transorber, the ultraviolet radiation transorber having an absorption maximum corresponding to a substantially single wavelength of ultraviolet radiation from an excimer lamp; and irradiating the colored composition with the excimer lamp to irreversibly mutate the colorant so that the colorant is substantially undetectable by the photo-sensing apparatus.

12. The method of claim 11, wherein the mutable colored composition is present on the first surface of the sheet in the form of indicia-receiving locations.

13. The method of claim 11, wherein the mutable colored composition is present on the first surface of the sheet in the form of indicia.

14. The method of claim 11, wherein the mutable colored composition further comprises a molecular includant.

15. The method of claim 14, wherein the molecular includant is selected from the group consisting of clathrates, zeolites, and cyclodextrins.

16. The method of claim 11, wherein the mutable colored composition is in the form of text or graphics.

17. The method of claim 11, wherein the form is a transmitted-read form or a reflective-read form.

18. The method of claim 11, wherein the carrier material is substantially opaque, transparent or translucent.

19. The method of claim 11, wherein the excimer lamp emits an incoherent, pulsed ultraviolet radiation having a substantially single wavelength from about 125 nanometers to about 360 nanometers.

20. A method of making a data processing form for use in photo-sensing apparatus which detect indicia at indicia-receiving locations on the form, the method comprising:

providing a substrate; and applying a mutable colored composition onto a surface of the substrate, wherein the mutable colored composition comprises a mutable colorant a molecular includant and an ultraviolet radiation transorber, the ultraviolet radiation transorber having an absorption maximum corresponding to a substantially single wavelength of ultraviolet radiation from an excimer lamp; the colored composition being irreversibly mutated and substantially undetectable by the photo-sensing apparatus upon irradiating with the excimer lamp.

21. The method of claim 20, wherein the mutable colored composition is present on the first surface of the sheet in the form of indicia-receiving locations.

22. The method of claim 20, wherein the mutable colored composition is present on the first surface of the sheet in the form of indicia.

23. The method of claim 20, wherein the molecular includant is selected from the group consisting of clathrates, zeolites, and cyclodextrins.

24. The method of claim 20, wherein the mutable colored composition is in the form of text or graphics.

25. The method of claim 20, wherein the form is a transmitted-read form or a reflective-read form.

26. The method of claim 20, wherein the carrier material is substantially opaque, transparent or translucent.

27. The method of claim 20, wherein the excimer lamp emits an incoherent, pulsed ultraviolet radiation having a substantially single wavelength from about 125 nanometers to about 360 nanometers.

28. The method of claim 20, wherein the molecular includant is covalently bonded to the ultraviolet radiation transorber.

* * * * *